US007259160B2

(12) United States Patent
Liang et al.

(10) Patent No.: US 7,259,160 B2
(45) Date of Patent: *Aug. 21, 2007

(54) HEXAHYDRODIAZEPINONES AS DIPEPTIDYL PEPTIDASE-IV INHIBITORS FOR THE TREATMENT OR PREVENTION OF DIABETES

(75) Inventors: Gui-Bai Liang, Scotch Plains, NJ (US); Tesfaye Biftu, Freehold, NJ (US); Danqing Dennis Feng, Branchburg, NJ (US); Ann E. Weber, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/566,235

(22) PCT Filed: Jul. 27, 2004

(86) PCT No.: PCT/US2004/024052

§ 371 (c)(1),
(2), (4) Date: Jan. 27, 2006

(87) PCT Pub. No.: WO2005/011581

PCT Pub. Date: Feb. 10, 2005

(65) Prior Publication Data

US 2006/0211682 A1 Sep. 21, 2006

Related U.S. Application Data

(60) Provisional application No. 60/491,606, filed on Jul. 31, 2003.

(51) Int. Cl.
C07D 243/08 (2006.01)
A61K 31/551 (2006.01)
A61P 3/10 (2006.01)

(52) U.S. Cl. .................. 514/218; 514/221; 540/492; 540/500

(58) Field of Classification Search ........... 540/492, 540/500; 514/218, 221
See application file for complete search history.

(56) References Cited

U.S. PATENT DOCUMENTS

| 4,386,090 | A | 5/1983 | Moinet et al. |
| 5,939,560 | A | 8/1999 | Jenkins et al. |
| 6,011,155 | A | 1/2000 | Villhauer |
| 6,166,063 | A | 12/2000 | Villhauer |
| 6,303,661 | B1 | 10/2001 | Demuth et al. |
| 6,432,969 | B1 | 8/2002 | Villhauer |
| 6,699,871 | B2 | 3/2004 | Edmondson et al. |

FOREIGN PATENT DOCUMENTS

| WO | WO97/40832 A1 | 11/1997 |
| WO | WO98/19998 A2 | 5/1998 |
| WO | WO98/19998 A3 | 5/1998 |
| WO | WO 00/34241 A1 | 6/2000 |
| WO | WO 01/34594 A1 | 5/2001 |
| WO | WO 01/42262 A2 | 6/2001 |
| WO | WO 01/96295 A2 | 12/2001 |
| WO | WO 01/96295 A3 | 12/2001 |
| WO | WO 02/02560 A2 | 1/2002 |
| WO | WO 02/02560 A3 | 1/2002 |
| WO | WO 02/076450 A1 | 10/2002 |
| WO | WO 03/000180 A2 | 1/2003 |
| WO | WO 03/000181 A2 | 1/2003 |
| WO | WO 03/000181 A3 | 1/2003 |
| WO | WO 2003/000180 A3 | 1/2003 |
| WO | WO 03/082817 A2 | 10/2003 |
| WO | WO 2004/007468 A1 | 1/2004 |
| WO | WO 2004/032836 A2 | 4/2004 |
| WO | WO 2004/032836 A3 | 4/2004 |
| WO | WO 2004/043940 A1 | 5/2004 |
| WO | WO 2004/050022 A2 | 6/2004 |
| WO | WO 2004/058266 A1 | 7/2004 |
| WO | WO 2004/064778 A2 | 8/2004 |
| WO | WO 2004/069162 A2 | 8/2004 |
| WO | WO 2004/110436 A1 | 12/2004 |
| WO | WO 2004/112701 A2 | 12/2004 |
| WO | WO 2004/112701 A3 | 12/2004 |
| WO | WO 2005/002530 A1 | 1/2005 |
| WO | WO 2005/011581 A2 | 2/2005 |
| WO | WO 2005/044195 A2 | 5/2005 |
| WO | WO 2005/056003 A1 | 6/2005 |
| WO | WO 2005/056013 A1 | 6/2005 |
| WO | WO 2005/108382 A1 | 11/2005 |
| WO | WO 2005/116029 A1 | 12/2005 |
| WO | WO 2005/123685 A1 | 12/2005 |
| WO | WO 2006/009886 A1 | 1/2006 |
| WO | WO 2006/023750 A2 | 3/2006 |

OTHER PUBLICATIONS

K. Augustyns, et al., "Inhibitors of proline-specific dipeptidyl peptidase: DPP IV inhibitors as a novel approach for the treatment of Type 2 diabetes", Expert Opin. Ther. Patents, vol. 15(10), pp. 1387-1407 (2005).
Hans-Ulrich Demuth, et al., "Type 2 diabetes—Therapy with dipeptidyl peptidase IV inhibitors", Biochimica et Biophysica Acta, vol. 1751, pp. 33-44 (2005).

*Primary Examiner*—Bruck Kifle
(74) *Attorney, Agent, or Firm*—Philippe L. Durette; Catherine D. Fitch

(57) ABSTRACT

The present invention is directed to hexahydrodiazepinone compounds which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

32 Claims, No Drawings

HEXAHYDRODIAZEPINONES AS DIPEPTIDYL PEPTIDASE-IV INHIBITORS FOR THE TREATMENT OR PREVENTION OF DIABETES

CROSS REFERENCE TO RELATED APPLICATIONS

This application is the National Stage of International Application No. PCT/US2004/024052, filed 27 Jul. 2004, which claims the benefit under 35 U.S.C. 119(e) of U.S. Provisional Application No. 60/491,606, filed 31 Jul. 2003.

FIELD OF THE INVENTION

The present invention relates to novel hexahydrodiazepinone compounds which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DPP-IV" or "DP-IV") enzyme are also under investigation as drugs that may be useful in the treatment of diabetes, and particularly type 2 diabetes. See for example WO 97/40832, WO 98/19998, U.S. Pat. No. 5,939,560, Bioorg. Med. Chem. Lett., 6: 1163-1166 (1996); and Bioorg. Med. Chem. Lett., 6: 2745-2748 (1996). The usefulness of DPP-IV inhibitors in the treatment of type 2 diabetes is based on the fact that DPP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DPP-IV leads to decreased inactivation of the incretins, and this in turn results in increased effectiveness of the incretins in stimulating production of insulin by the pancreas. DPP-IV inhibition therefore results in an increased level of serum insulin. Advantageously, since the incretins are produced by the body only when food is consumed, DPP-IV inhibition is not expected to increase the level of insulin at inappropriate times, such as between meals, which can lead to excessively low blood sugar (hypoglycemia). Inhibition of DPP-IV is therefore expected to increase insulin without increasing the risk of hypoglycemia, which is a dangerous side effect associated with the use of insulin secretagogues.

DPP-IV inhibitors also have other therapeutic utilities, as discussed herein. DPP-IV inhibitors have not been studied extensively to date, especially for utilities other than diabetes. New compounds are needed so that improved DPP-IV inhibitors can be found for the treatment of diabetes and potentially other diseases and conditions. The therapeutic potential of DPP-IV inhibitors for the treatment of type 2 diabetes is discussed by D. J. Drucker in *Exp. Opin. Invest. Drugs*, 12: 87-100 (2003) and by K. Augustyns, et al., in *Exp. Opin. Ther. Patents*, 13: 499-510 (2003).

SUMMARY OF THE INVENTION

The present invention is directed to novel hexahydrodiazepinone compounds which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to hexahydrodiazepinone compounds useful as inhibitors of dipeptidyl peptidase-IV. Compounds of the present invention are described by structural formula I:

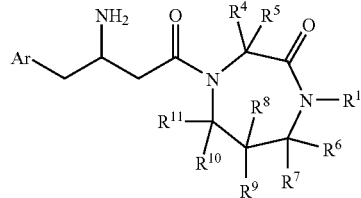

(I)

or a pharmaceutically acceptable salt thereof; wherein
each n is independently 0, 1, or 2;
Ar is phenyl substituted with one to five $R^3$ substituents;
$R^1$ is selected from the group consisting of hydrogen,
  $C_{1-10}$ alkyl, wherein alkyl is unsubstituted or substituted with one to five substituents independently selected from halogen, hydroxy, $C_{1-6}$ alkoxy, carboxy, $C_{1-6}$ allyloxycarbonyl, and phenyl-$C_{1-3}$ alkoxy, wherein alkoxy is unsubstituted or substituted with one to five halogens,
  $(CH_2)_n$-aryl, wherein aryl is unsubstituted or substituted with one to five substituents independently selected from halogen, CN, hydroxy, $R^2$, $OR^2$, $NHSO_2R^2$, $NR^2SO_2R^2$, $SO_2R^2$, $CO_2H$, and $C_{1-6}$ alkyloxycarbonyl,
  $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens,
  $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
  $(CH_2)_n$-$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens; and
  wherein any methylene ($CH_2$) carbon atom in $(CH_2)_n$ is unsubstituted or substituted with one to two groups independently selected from halogen, hydroxy, and $C_{1-4}$ alkyl unsubstituted or substituted with one to five halogens;

each $R^3$ is independently selected from the group consisting of
hydrogen,
halogen,
cyano,
hydroxy,
$C_{1-6}$ alkyl, unsubstituted or substituted with one to five halogens,
$C_{1-6}$ alkoxy, unsubstituted or substituted with one to five halogens,
carboxy,
alkoxycarbonyl,
amino,
$NHR^2$,
$NR^2R^2$,
$NHSO_2R^2$,
$NR^2SO_2R^2$,
$NHCOR^2$,
$NR^2COR^2$,
$NHCO_2R^2$,
$NR^2CO_2R^2$,
$SO_2R^2$,
$SO_2NH_2$,
$SO_2NHR^2$, and
$SO_2NR^2R^2$;

each $R^2$ is independently $C_{1-6}$ alkyl, unsubstituted or substituted with one to five substituents independently selected from halogen, $CO_2H$, and $C_{1-6}$ alkyloxycarbonyl;

$R^4$, $R^6$, and $R^{10}$ are each independently selected from the group consisting of:
hydrogen,
cyano,
carboxy,
$C_{1-6}$ alkyloxycarbonyl,
  $C_{1-10}$ alkyl, unsubstituted or substituted with one to five substituents independently selected from halogen, hydroxy, $C_{1-6}$ alkoxy, carboxy, $C_{1-6}$ alkyloxycarbonyl, and phenyl-$C_{1-3}$ alkoxy, wherein alkoxy is unsubstituted or substituted with one to five halogens,
  $(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens,
  $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, (CH$_2$)$_n$-heterocyclyl, wherein heterocyclyl is unsubstituted or substituted with one to three substituents independently selected from oxo, hydroxy, halogen, C$_{1-6}$ alkyl, and C$_{1-6}$ alkoxy, wherein alkyl and alkoxy are unsubstituted or substituted with one to five halogens, (CH$_2$)$_n$—C$_{3-6}$ cycloalkyl, wherein cycloalkyl is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens, (CH$_2$)$_n$CONR$^{12}$R$^{13}$, wherein R$^{12}$ and R$^{13}$ are independently selected from the group consisting of hydrogen, tetrazolyl, thiazolyl, (CH$_2$)$_n$-phenyl, (CH$_2$)$_n$—C$_{3-6}$ cycloalkyl, and C$_{1-6}$ alkyl, wherein alkyl is unsubstituted or substituted with one to five halogens and wherein phenyl and cycloalkyl are unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens; or wherein R$^{12}$ and R$^{13}$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens;

and wherein any methylene (CH$_2$) carbon atom in (CH$_2$)$_n$ is unsubstituted or substituted with one to two groups independently selected from halogen, hydroxy, and C$_{1-4}$ alkyl unsubstituted or substituted with one to five halogens;

R$^8$ is selected from the group consisting of halogen, hydroxy, and R$^4$;

R$^5$, R$^7$ and R$^{11}$ are each independently hydrogen or C$_{1-6}$ alkyl; or wherein R$^7$ and R$^1$ together with the nitrogen atom to which R$^1$ is attached form a heterocyclic ring selected from azetidine, pyrrolidine and piperidine wherein said heterocyclic ring is unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens; and R$^9$ is selected from the group consisting of hydrogen, hydroxy, halogen, or C$_{1-6}$ alkyl;

with the proviso that at least one of R$^6$, R$^7$, R$^8$ and R$^9$ is not hydrogen.

In one embodiment of the compounds of the present invention, the carbon atom marked with an * has the R configuration as depicted in formula Ia

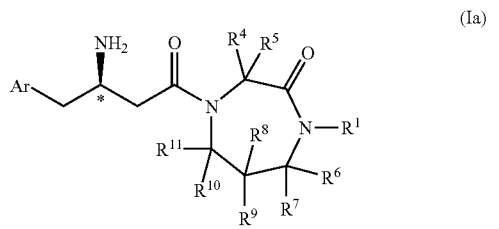

(Ia)

wherein Ar, R$^1$, R$^4$, R$^5$, R$^6$, R$^7$, R$^8$, R$^9$, R$^{10}$, and R$^{11}$ are as defined herein.

In a second embodiment of the compounds of the present invention, R$^3$ is selected from the group consisting of hydrogen, fluoro, chloro, bromo, trifluoromethyl, and methyl. In a class of this embodiment, R$^3$ is selected from the group consisting of hydrogen, fluoro, and chloro. In a subclass of this class, R$^3$ is hydrogen or fluoro.

In a third embodiment of the compounds of the present invention, R$^1$ is selected from the group consisting of:
hydrogen,
C$_{1-6}$ alkyl, wherein alkyl is unsubstituted or substituted with one to five substituents independently selected from halogen, hydroxy, C$_{1-6}$ alkoxy, carboxy, C$_{1-6}$ alkyloxycarbonyl, and phenyl-C$_{1-3}$ alkoxy, wherein alkoxy is unsubstituted or substituted with one to five halogens, and
(CH$_2$)$_n$—C$_{3-6}$ cycloalkyl, wherein cycloalkyl is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens; and
wherein any methylene (CH$_2$) carbon atom in (CH$_2$)$_n$ is unsubstituted or substituted with one to two groups independently selected from halogen, hydroxy, and C$_{1-4}$ alkyl unsubstituted or substituted with one to five halogens.

In a class of this embodiment of the compounds of the present invention, R$^1$ is selected from the group consisting of
hydrogen,
methyl, and
cyclopropyl.

In a subclass of this class, R$^1$ is hydrogen.

In a fourth embodiment of the compounds of the present invention, R$^4$ is selected from the group consisting of:
hydrogen,
C$_{1-6}$ alkyl, unsubstituted or substituted with one to five substituents independently selected from halogen, hydroxy, C$_{1-6}$ alkoxy, carboxy, C$_{1-6}$ alkyloxycarbonyl, and phenyl-C$_{1-3}$ alkoxy, wherein alkoxy is unsubstituted or substituted with one to five halogens,
(CH$_2$)$_n$-aryl, wherein aryl is unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens,
(CH$_2$)$_n$-heteroaryl, wherein heteroaryl is unsubstituted or substituted with one to three substituents independently selected from hydroxy, halogen, C$_{1-6}$ alkyl, and C$_{1-6}$ alkoxy, wherein alkyl and alkoxy are unsubstituted or substituted with one to five halogens,
(CH$_2$)$_n$—C$_{3-6}$ cycloalkyl, wherein cycloalkyl is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens; and
wherein any methylene (CH$_2$) carbon atom in (CH$_2$)$_n$ is unsubstituted or substituted with one to two groups independently selected from halogen, hydroxy, and C$_{1-4}$ alkyl unsubstituted or substituted with one to five halogens.

In a class of this embodiment, R$^4$ is selected from the group consisting of:
hydrogen,
CH$_3$,
CH$_2$CH$_3$,
CH$_2$CF$_3$, CH$_2$(2-pyridyl),
CH$_2$Ph,
CH$_2$(2-F-Ph),
CH$_2$(2-Me-Ph), and
CH$_2$(2-CF$_3$-Ph).

In a fifth embodiment of the compounds of the present invention, R$^6$ is selected from the group consisting of:
hydrogen,
C$_{1-6}$ alkyl, unsubstituted or substituted with one to five substituents independently selected from halogen, hydroxy, C$_{1-6}$ alkoxy, carboxy, C$_{1-6}$ alkyloxycarbonyl, and phenyl-C$_{1-3}$ alkoxy, wherein alkoxy is unsubstituted or substituted with one to five halogens,
(CH$_2$)$_n$-aryl, wherein aryl is unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens,
(CH$_2$)$_n$-heteroaryl, wherein heteroaryl is unsubstituted or substituted with one to three substituents independently selected from hydroxy, halogen, C$_{1-6}$ alkyl, and C$_{1-6}$ alkoxy, wherein alkyl and alkoxy are unsubstituted or substituted with one to five halogens,
(CH$_2$)$_n$—C$_{3-6}$ cycloalkyl, wherein cycloalkyl is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens; and
wherein any methylene (CH$_2$) carbon atom in (CH$_2$)$_n$ is unsubstituted or substituted with one to two groups independently selected from halogen, hydroxy, and C$_{1-4}$ alkyl unsubstituted or substituted with one to five halogens.

In a class of this embodiment, R$^6$ is selected from the group consisting of:
hydrogen,
C$_{1-6}$ alkyl, unsubstituted or substituted with one to five substituents independently selected from halogen, hydroxy, C$_{1-6}$ alkoxy, carboxy, C$_{1-6}$ alkyloxycarbonyl, and phenyl-C$_{1-3}$ alkoxy, wherein alkoxy is unsubstituted or substituted with one to five halogens, and
(CH$_2$)$_n$-aryl, wherein aryl is unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens; and
wherein methylene (CH$_2$) carbon atom in (CH$_2$)$_n$ is unsubstituted or substituted with one to two groups independently selected from halogen, hydroxy, and C$_{1-4}$ alkyl unsubstituted or substituted with one to five halogens.

In a subclass of this class, R$^6$ is selected from the group consisting of:
hydrogen,
CH$_3$,
CH$_2$CH$_3$,
CF$_3$,
CH$_2$Ph, and
CH$_2$(2-F-Ph).

In a sixth embodiment of the compounds of the present invention, R$^8$ is selected from the group consisting of:
hydrogen,
hydroxy,
halogen, and
C$_{1-6}$ alkyl, unsubstituted or substituted with one to five substituents independently selected from halogen, hydroxy, C$_{1-6}$ alkoxy, carboxy, C$_{1-6}$ alkyloxycarbonyl, and phenyl-C$_{1-3}$ alkoxy, wherein alkoxy is unsubstituted or substituted with one to five halogens.

In a class of this embodiment, R$^8$ is hydrogen.

In a seventh embodiment of the compounds of the present invention, R$^{10}$ is selected from the group consisting of:
hydrogen, and
C$_{1-6}$ alkyl, unsubstituted or substituted with one to five substituents independently selected from halogen, hydroxy, C$_{1-6}$ alkoxy, carboxy, C$_{1-6}$ alkyloxycarbonyl, and phenyl-C$_{1-3}$ alkoxy, wherein alkoxy is unsubstituted or substituted with one to five halogens.

In a class of this embodiment, R$^{10}$ is hydrogen.

In an eighth embodiment of the compounds of the present invention, R$^5$, R$^7$ and R$^{11}$ are each independently selected from hydrogen and methyl.

In a class of this embodiment, R$^5$, R$^7$ and R$^{11}$ are hydrogen.

In a ninth embodiment of the compounds of the present invention, R$^9$ is selected from hydrogen, halogen and methyl.

In a class of this embodiment, R$^9$ is hydrogen.

In a further class of this embodiment, R$^9$ is methyl and R$^5$, R$^7$, R$^8$, R$^{10}$, and R$^{11}$ are hydrogen. In a subclass of this class, R$^4$ is selected from the group consisting of:
hydrogen,
CH$_3$,
CH$_2$CH$_3$,
CH$_2$CF$_3$,
CH$_2$(2-pyridyl),
CH$_2$Ph,
CH$_2$(2-F-Ph),
CH$_2$(2-Me-Ph), and
CH$_2$(2-CF$_3$-Ph).

In a tenth embodiment of the compounds of the present invention, R$^5$, R$^7$, R$^8$, R$^9$, R$^{10}$, and R$^{11}$ are hydrogen, with the proviso that R$^6$ is not hydrogen. In a class of this embodiment, R$^4$ is selected from the group consisting of:
hydrogen,
CH$_3$,
CH$_2$CH$_3$,
CH$_2$CF$_3$,
CH$_2$(2-pyridyl),
CH$_2$Ph,
CH$_2$(2-F-Ph),
CH$_2$(2-Me-Ph), and
CH$_2$(2-CF$_3$-Ph); and
R$^6$ is selected from the group consisting of:
CH$_3$,
CH$_2$CH$_3$,
CF$_3$,
CH$_2$Ph, and
CH$_2$(2-F-Ph).

In a subclass of this class, R¹ is hydrogen.

In a subclass of this subclass, the stereogenic carbon atoms marked with an  and an * have the stereochemistry as depicted in formula Ib:

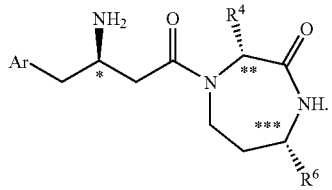

(Ib)

In an eleventh embodiment of the compounds of the present invention, R⁷ and R¹ together with the nitrogen atom to which R¹ is attached form a heterocyclic ring selected from azetidine, pyrrolidine and piperidine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens.

In a class of this embodiment, R⁷ and R¹ together with the nitrogen atom to which R¹ is attached form a pyrrolidine ring. In a subclass of this class, R⁴ is selected from the group consisting of:
hydrogen,
$CH_3$,
$CH_2CH_3$,
$CH_2CF_3$,
$CH_2$(2-pyridyl),
$CH_2Ph$,
$CH_2$(2-F-Ph),
$CH_2$(2-Me-Ph), and
$CH_2$(2-CF3-Ph).

Illustrative, but nonlimiting, examples of compounds of the present invention that are inhibitors of dipeptidyl peptidase-IV are the following:

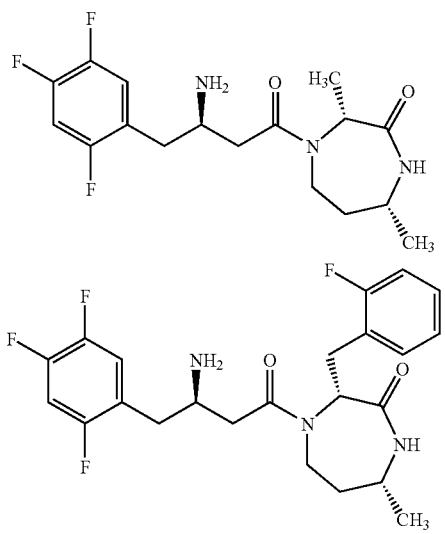

-continued

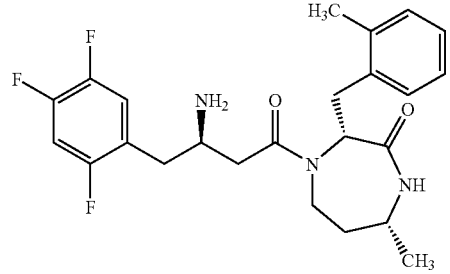

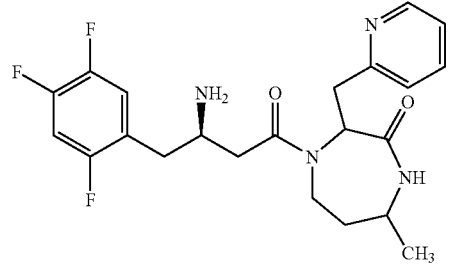

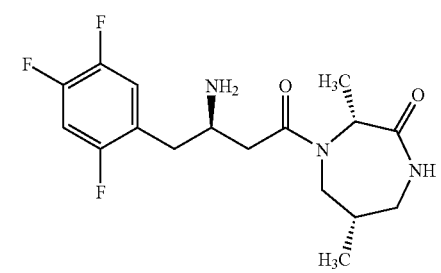

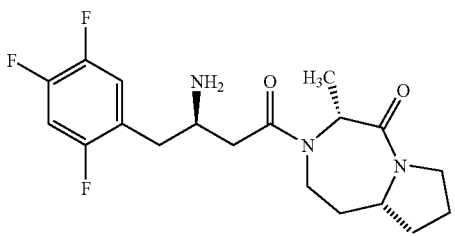

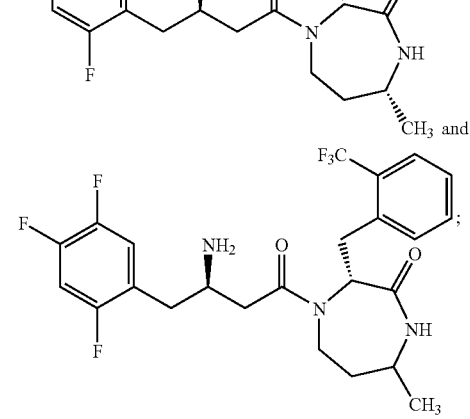

or a pharmaceutically acceptable salt thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.)].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are mono-cyclic or bicyclic 6-10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further including the oxidized forms of sulfur, namely SO and SO$_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-α]pyridinyl, [1,2,4-triazolo][4,3-α]pyridinyl, pyrazolo[1,5-α]pyridinyl, [1,2,4-triazolo][1,5-α]pyridinyl, 2-oxo-1,3-benzoxazolyl, 4-oxo-3H-quinazolinyl, 3-oxo-[1,2,4]-triazolo[4,3-α]-2H-pyridinyl, 5-oxo-[1,2,4]-4H-oxadiazolyl, 2-oxo-[1,3,4]-3H-oxadiazolyl, 2-oxo-1,3dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. CF$_3$O and CF$_3$CH$_2$O).

The compounds of the present invention may contain one or more asymmetric centers and can thus occur as racemates and racemic mixtures, single enantiomers, diastereomeric mixtures and individual diastereomers. In particular the compounds of the present invention have an asymmetric center at the carbon atom marked with an * in formula Ia and at the carbon atoms marked with an *, , and * in formula Ib. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia shows the preferred sterochemistry at the carbon atom to which is attached the amino group of the beta-amino acid from which these compounds are prepared. Formula Ib shows the preferred sterochemistry at the carbon atom to which is attached the amino group of the beta-amino acid from which these compounds are prepared and at two of the stereogenic carbon atoms of the hexahydrodiazepinone ring.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DPP-IV to release the fluorescent AMC leaving group. The kinetic parameters that describe this reaction are as follows: $K_m=50$ µM; $k_{cat}=75$ s$^{-1}$; $k_{cat}/K_m=1.5\times10^6$ M$^{-1}$s$^{-1}$. A typical reaction contains approximately 50 µM enzyme, 50 µM. Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 µM. Such a result is indicative of the intrinsic activity of the compounds in use as inhibitors the dipeptidyl peptidase-IV enzyme activity.

Dipeptidyl peptidase-IV enzyme (DPP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DPP-WV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DPP-IV. Studies with DPP-IV$^{(-/-)}$-deficient mice and preliminary clinical trials indicate that DPP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DPP-IV (eg. PACAP). Inactivation of these peptides by DPP-IV may also play a role in glucose homeostasis. The DPP-IV inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DPP-IV inhibitors may also be useful to treat hypertension associated with this condition.

Obesity: DPP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine*, 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DPP-IV. ICV administration of GLP-2 also inhibits food intake, analogous to the effects observed with GLP-1 (*Nature Medicine*, 6: 802-807 (2000)). In addition, studies with DPP-IV deficient mice suggest that these animals are resistant to diet-induced obesity and associated pathology (e.g. hyperinsulinonemia).

Growth Hormone Deficiency: DPP-IV inhibition may be useful for the treatment of growth hormone deficiency, based on the hypothesis that growth-hormone releasing factor (GRF), a peptide that stimulates release of growth hormone from the anterior pituitary, is cleaved by the DPP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF [344]; this is prevented by the DPP-IV inhibitor diprotin A; and (3) GRF[3-44] is found in the plasma of a human GRF transgenic pig (*J. Clin. Invest.*, 83: 1533-1540 (1989)). Thus DPP-IV inhibitors may be useful for the same spectrum of indications which have been considered for growth hormone secretagogues.

Intestinal Injury: The potential for using DPP-IV inhibitors for the treatment of intestinal injury is suggested by the results of studies indicating that glucagon-like peptide-2 (GLP-2), a likely endogenous substrate for DPP-IV, may exhibit trophic effects on the intestinal epithelium (*Regulatory Peptides*, 90: 27-32 (2000)). Administration of GLP-2 results in increased small bowel mass in rodents and attenuates intestinal injury in rodent models of colitis and enteritis.

Immunosuppression: DPP-IV inhibition may be useful for modulation of the immune response, based upon studies implicating the DPP-IV enzyme in T cell activation and in chemokine processing, and efficacy of DPP-IV inhibitors in in vivo models of disease. DPP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DPP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DPP-IV hydrolysis.

DPP-IV inhibitors have been shown to be efficacious immunosuppressants in animal models of transplantation and arthritis. Prodipine (Pro-Pro-diphenyl-phosphonate), an irreversible inhibitor of DPP-IV, was shown to double cardiac allograft survival in rats from day 7 to day 14 (*Transplantation*, 63: 1495-1500 (1997)). DPP-IV inhibitors have been tested in collagen and alkyldiamine-induced arthritis in rats and showed a statistically significant attenuation of hind paw swelling in this model [*Int. J. Immunopharmacology*, 19:15-24 (1997) and *Immunopharmacology*, 40: 21-26 (1998)]. DPP-IV is upregulated in a number of autoimmune diseases including rheumatoid arthritis, multiple sclerosis, Graves' disease, and Hashimoto's thyroiditis (*Immunology Today*, 20: 367-375 (1999)).

HIV Infection: DPP-IV inhibition may be useful for the treatment or prevention of HIV infection or AIDS because a number of chemokines which inhibit HIV cell entry are potential substrates for DPP-IV (*Immunology Today* 20: 367-375 (1999)). In the case of SDF-1alpha, cleavage decreases antiviral activity (*PNAS*, 95: 6331-6 (1998)). Thus, stabilization of SDF-1alpha through inhibition of DPP-IV would be expected to decrease HIV infectivity.

Hematopoiesis: DPP-IV inhibition may be useful for the treatment or prevention of hematopiesis because DPP-IV may be involved in hematopoiesis. A DPP-IV inhibitor, Val-Boro-Pro, stimulated hematopoiesis in a mouse model of cyclophosphamide-induced neutropenia (WO 99/56753).

Neuronal Disorders: DPP-IV inhibition may be useful for the treatment or prevention of various neuronal or psychiatric disorders because a number of peptides implicated in a variety of neuronal processes are cleaved in vitro by DPP-IV. A DPP-IV inhibitor thus may have a therapeutic benefit in the treatment of neuronal disorders. Endomorphin-2, beta-casomorphin, and substance P have all been shown to be in vitro substrates for DPP-IV. In all cases, in vitro cleavage is highly efficient, with $k_{cat}/K_m$ about $10^6$ $M^{-1}s^{-1}$ or greater. In an electric shock jump test model of analgesia in rats, a DPP-IV inhibitor showed a significant effect that was independent of the presence of exogenous endomorphin-2 (*Brain Research*, 815: 278-286 (1999)).

Neuroprotective and neuroregenerative effects of DPP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26-29, 2002 (Berlin, Germany)].

Cardiovascular Disease: GLP-1 has been shown to be beneficial when administered to patients following acute myocardial infarction, leading to improved left ventricular function and reduced mortality after primary angioplasty (Circulation, 109: 962-965 (2004)). GLP-1 administration is also useful for the treatment of left ventricular systolic dysfunction in dogs with dilated cardiomyopathy and ischemic induced left ventricular dysfunction, and thus may prove useful for the treatment of patients with heart failure (US2004/0097411). DPP-IV inhibitors are expected to show similar effects through their ability to stabilize endogenous GLP-1.

Tumor Invasion and Metastasis: DPP-IV inhibition may be useful for the treatment or prevention of tumor invasion and metastasis because an increase or decrease in expression of several ectopeptidases including DPP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DPP-IV expression has been observed on T cell lymphoma, T cell acute lymphoblastic leukemia, cell-derived thyroid carcinomas, basal cell carcinomas, and breast carcinomas. Thus, DPP-IV inhibitors may have utility in the treatment of such carcinomas.

Benign Prostatic Hypertrophy: DPP-IV inhibition may be useful for the treatment of benign prostatic hypertrophy because increased DPP-IV activity was noted in prostate tissue from patients with BPH (*Eur. J. Clin. Chem. Clin. Biochem.*, 30: 333-338 (1992)).

Sperm motility/male contraception: DPP-IV inhibition may be useful for the altering sperm motility and for male contraception because in seminal fluid, prostatosomes, prostate derived organelles important for sperm motility, possess very high levels of DPP-IV activity (*Eur. J. Clin. Chem. Clin. Biochem.*, 30: 333-338 (1992)).

Gingivitis: DPP-IV inhibition may be useful for the treatment of gingivitis because DPP-IV activity was found in gingival crevicular fluid and in some studies correlated with periodontal disease severity (*Arch. Oral Biol.*, 37: 167-173 (1992)).

Osteoporosis: DPP-IV inhibition may be useful for the treatment or prevention of osteoporosis because GIP receptors are present in osteoblasts.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DPP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DPP-IV) inhibitors;

(b) insulin sensitizers including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide glyburide, glipizide, glimepiride, and meglitinides, such as repaglinide;

(e) α-glucosidase inhibitors (such as acarbose and miglitol);

(f) glucagon receptor antagonists such as those disclosed in WO 98/04528, WO 99/01423, WO 00/39088, and WO 00/69810;

(g) GLP-1, GLP-1 mimetics, and GLP-1 receptor agonists such as those disclosed in WO00/42026 and WO00/59887;

(h) GIP and GIP mimetics such as those disclosed in WO00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as beta-sitosterol and ezetimibe, (vii) acyl CoA:cholesterol acyltransferase inhibitors, such as avasimibe, and (viii) anti-oxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, and melanin-concentrating hormone (MCH) receptor antagonists;

(m) ileal bile acid transporter inhibitors;

(n) agents intended for use in inflammatory conditions such as aspirin, non-steroidal anti-inflammatory drugs, glucocorticoids, azulfidine, and selective cyclooxygenase-2 inhibitors;

(o) antihypertensive agents such as ACE inhibitors (enalapril, lisinopril, captopril, quinapril, tandolapril), A-II receptor blockers (losartan, candesartan, irbesartan, valsartan, telmisartan, eprosartan), beta blockers and calcium channel blockers; and (p) glucokinase activators (GKAs) such as those disclosed in WO 03/015774;

(q) inhibitors of 11β-hydroxysteroid dehydrogenase type 1, such as those disclosed in U.S. Pat. No. 6,730,690; and (r) inhibitors of cholesteryl ester transfer protein (CETP), such as torcetrapib.

Dipeptidyl peptidase-IV inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DPP-IV inhibitor compounds include isoleucine thiazolidide(P32/98); NVP-DPP-728; LAF 237; P93/01; and BMS 477118.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001) and D. Spanswick and K. Lee, "Emerging antiobesity drugs," *Expert Opin. Emerging Drugs*, 8: 217-237 (2003).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. Nos. 5,532,237; and 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists," *Expert Opin. Ther. Patents,* 12: 1631-1638 (2002).

The potential utility of safe and effective activators of glucokinase (GKAs) for the treatment of diabetes is discussed in J. Grimsby et al., "Allosteric Activators of Glucokinase: Potential Role in Diabetes Therapy," *Science,* 301: 370-373 (2003).

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared from beta amino acid intermediates such as those of formula II and substituted hexahydrodiazepinone intermediates such as those of formula m, using standard peptide coupling conditions followed by deprotection. The preparation of these intermediates is described in the following Schemes.

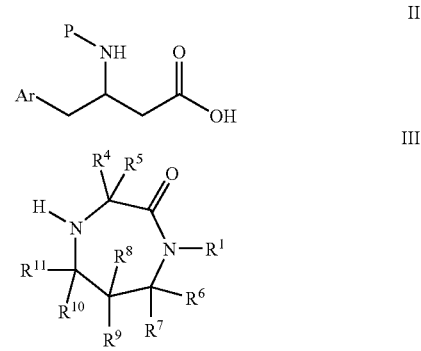

wherein Ar, $R^1$, $R^4$, $R^5$, $R^6$, $R^7$, $R^8$, $R^9$, $R^{10}$, and $R^{11}$ are as defined above and P is a suitable nitrogen protecting group such as tert-butoxycarbonyl (BOC), benzyloxycarbonyl (Cbz), or 9-fluorenylmethoxycarbonyl (Fmoc).

SCHEME 1

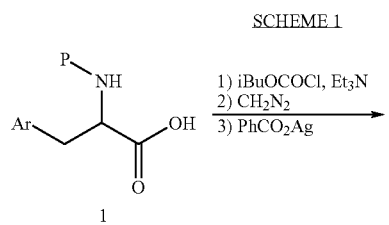

Compounds of formula II are commercially available, known in the literature or may be conveniently prepared by a variety of methods familiar to those skilled in the art. One common route is illustrated in Scheme 1. Protected alpha-amino acid 1, which may be commercially available or readily prepared from the corresponding amino acid by protection using, for example, di-tert-butyl dicarbonate (for P=BOC), carbobenzyloxy chloride (for P=Cbz), or N-(9-fluorenylmethoxycarbonyloxy)succinimide (for P=Fmoc), is treated with isobutyl chloroformate and a base such as triethylamine or diisopropylethylamine, followed by diazomethane. The resultant diazoketone is then treated with silver benzoate in a solvent such as methanol or aqueous dioxane and may be subjected to sonication following the procedure of Sewald et al., *Synthesis,* 837 (1997) in order to provide the beta amino acid II. As will be understood by those skilled in the art, for the preparation of enantiomerically pure beta amino acids II, enantiomerically pure alpha amino acids 1 may be used. Alternate routes to the protected beta-amino acid intermediates II can be found in the following reviews: E. Juaristi, *Enantioselective Synthesis of β-Amino Acids,* Ed., Wiley-VCH, New York: 1997; Juaristi et al., *Aldrichimica Acta,* 27: 3 (1994); and Cole et al., *Tetrahedron,* 32: 9517 (1994).

SCHEME 2

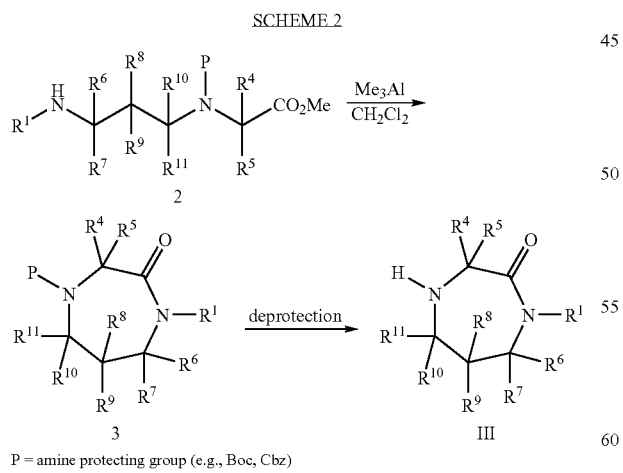

P = amine protecting group (e.g., Boc, Cbz)

Compounds of formula III are commercially available, known in the literature or may be conveniently prepared by a variety of methods familiar to those skilled in the art. One convenient method is shown in Scheme 2. Amino ester 2 is cyclized to N-protected hexahydrodiazepinone 3 using trimethylaluminum Deprotection, for example, in the case of Boc, by treatment with acid such as hydrogen chloride in dioxane or trifluoroacetic acid in dichloromethane, provides Intermediate III.

SCHEME 3

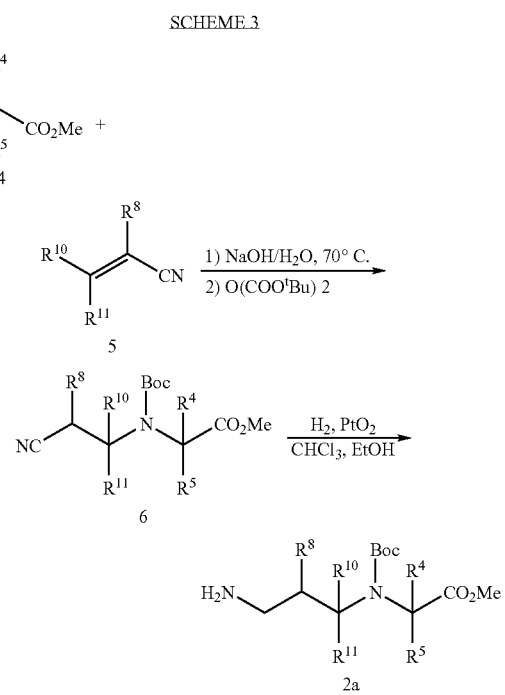

Amino esters 2 are known in the literature or may be conveniently prepared by a variety of methods familiar to those skilled in the art. One convenient method wherein $R^1$, $R^6$, $R^7$, and $R^9$ are hydrogen and P is a Boc group is shown in Scheme 3. Amino ester 4, conveniently used as its hydrochloride salt, is condensed with acrylonitrile 5 and the amino group of the product formed is protected, for example, as its tert-butoxycarbonyl (Boc) derivative, to provide 6. Reduction of the nitrile group, for example, by treatment with hydrogen using a catalyst such as platinum oxide, provides amine 2a.

SCHEME 4

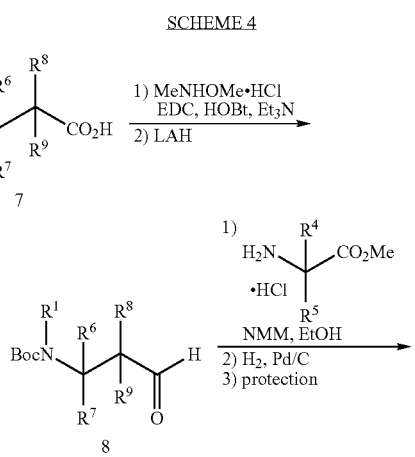

cyclized to hexahydrodiazepinone III with a reducing agent such as platinum oxide and hydrogen.

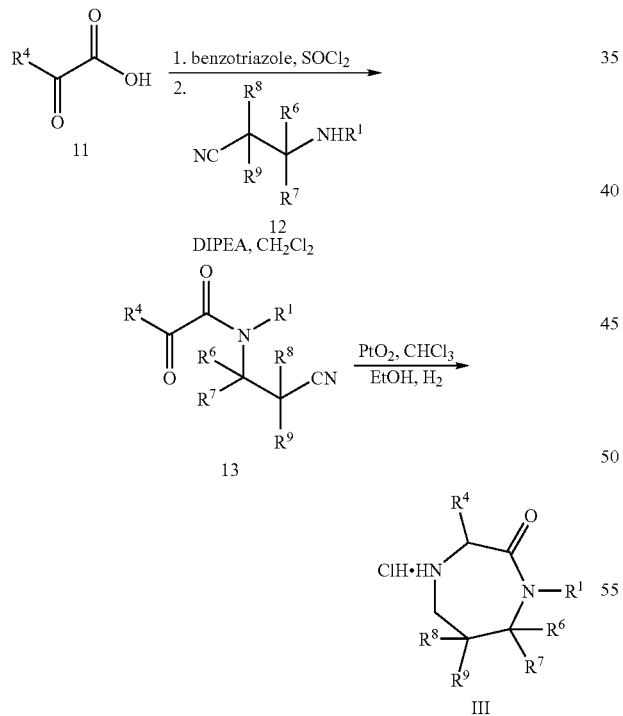

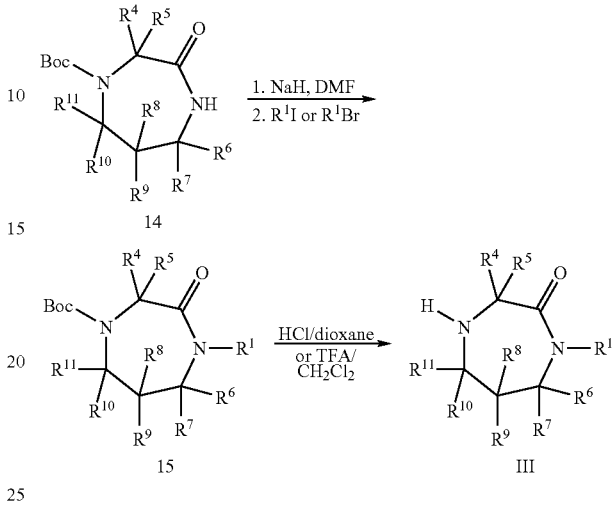

Another such method for the preparation of amine 2 wherein $R^{10}$ and $R^{11}$ are hydrogen is illustrated in Scheme 4. Amino acid 7 is coupled with N,O-dimethylamine, conveniently using a coupling reagent such as EDC/HOBt, and the resultant Weinreb amide is reduced to provide aldehyde 8. The aldehyde is treated with amino ester 9 and the corresponding imine reduced, for example, under catalytic hydrogenation conditions. The resultant secondary amine is then protected, for example as its Cbz derivative, to provide ester 10 (P=Cbz). Deprotection of the terminal amino group gives the desired intermediate 2b.

Hexahydrodiazepinone intermediates III and intermediates for their synthesis can be modified in various ways. For example, the amide nitrogen of intermediate 14, prepared as described for Intermediate 3 (Scheme 2) wherein $R^1$ is hydrogen, can be alkylated by deprotonation with a base such as sodium hydride followed by treatment with an alkyl halide as shown in Scheme 6. Deprotection of the resulting intermediate 15 provides intermediate III.

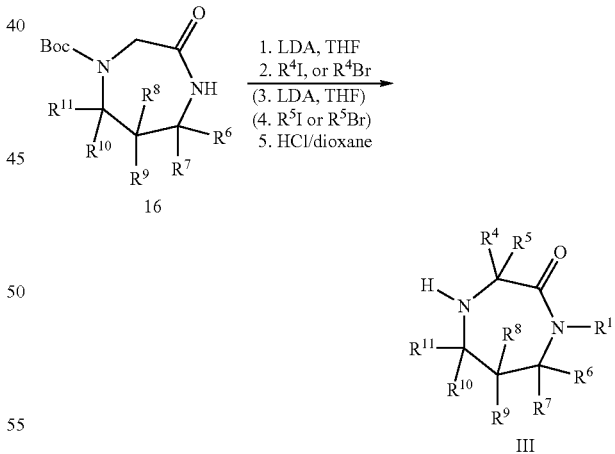

An alternate method of preparing hexahydrodiazepinone III wherein $R^5$, $R^{10}$, and $R^{11}$ are hydrogen is shown in Scheme 5. α-Ketoacids 11 such as pyruvic acid can be condensed with an aminopropionitrile 12 to provide the cyanoethyl oxopropanamides 13, which can be reductively Another such example is illustrated in Scheme 7. Protected hexahydrodiazepinone 16, wherein $R^4$ and/or $R^5$ is hydrogen, which may be prepared as described for Intermediate 15 in Scheme 6 or by protection of intermediate III, can be alkylated by deprotonation with a strong base such as LDA followed by treatment with an alkyl halide. The process may be repeated to install a second alkyl group, $R^5$. Deprotection provides Intermediate III.

SCHEME 8

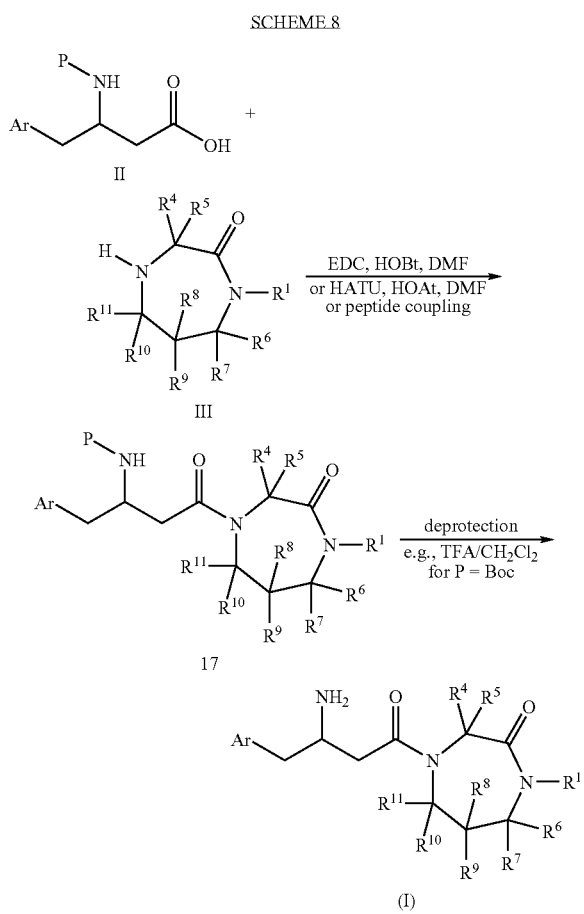

Intermediates II and III are coupled under standard peptide coupling conditions, for example, using 1-ethyl-3-(3-dimethylaminopropyl)carbodiimide and 1-hydroxybenzotriazole (EDC/HOBT) or O-(7-azabenzotriazol-1-yl)-N,N,N',N'-tetramethyluronium hexafluorophosphate and 1-hydroxy-7-azabenzotriazole (HATU/HOAT) in a solvent such as N,N-dimethylformamide (DMF) or dichloromethane for 3 to 48 hours at ambient temperature to provide Intermediate 17 as shown in Scheme 8. In some cases, Intermediate III may be a salt, such as a hydrochloride or trifluoroacetic acid salt, and in these cases it is convenient to add a base, generally N,N-diisopropylethylamine, to the coupling reaction. The protecting group is then removed with, for example, trifluoroacetic acid or methanolic hydrogen chloride in the case of Boc to give the desired amine I. The product is purified, if necessary, by recrystallization, trituration, preparative thin layer chromatography, flash chromatography on silica gel, such as with a Biotage® apparatus, or HPLC. Compounds that are purified by HPLC may be isolated as the corresponding salt. Purification of intermediates is achieved in the same manner.

In some cases the product I or synthetic intermediates illustrated in the above schemes may be further modified, for example, by manipulation of substituents on Ar, $R^1$, $R^4$, $R^5$, $R^6$, $R^7$, $R^8$, $R^9$, $R^{10}$, or $R^{11}$. These manipulations may include, but are not limited to, reduction, oxidation, alkylation, acylation, and hydrolysis reactions that are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

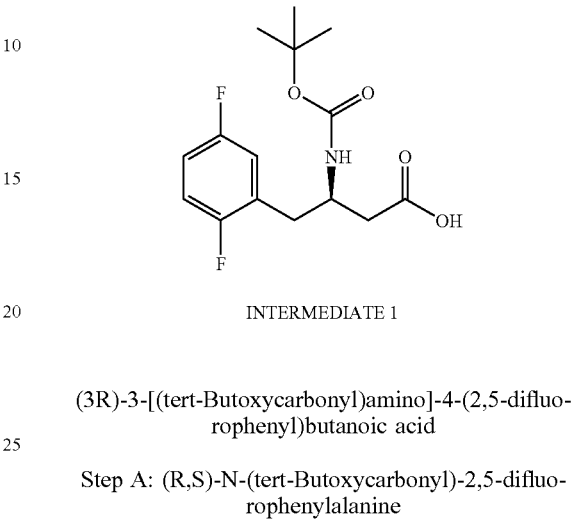

INTERMEDIATE 1

(3R)-3-[(tert-Butoxycarbonyl)amino]-4-(2,5-difluorophenyl)butanoic acid

Step A: (R,S)-N-(tert-Butoxycarbonyl)-2,5-difluorophenylalanine

To a solution of 0.5 g (2.49 mmol) of 2,5-difluoro-DL-phenylalanine in 5 mL of tert-butanol were added sequentially 1.5 mL of 2N aqueous sodium hydroxide solution and 543 mg of di-tert-butyl dicarbonate. The reaction was stirred at ambient temperature for 16 h and diluted with ethyl acetate. The organic phase was washed sequentially with 1N hydrochloric acid and aqueous brine solution, dried over magnesium sulfate and concentrated in vacuo. The crude material was purified by flash chromatography (silica gel, 97:2:1 dichloromethane:methanol:acetic acid) to afford the title compound. LC/MS 302 (M+1).

Step B: (R,S)-3-[(tert-Butoxycarbonyl)amino]-1-diazo-4-(2,5-difluoro-phenyl)butan-2-one To a solution of 2.23 g (7.4 mmol) of (R,S)-N-(tert-butoxycarbonyl)-2,5-difluorophenylalanine in 100 mL of diethyl ether at 0° C. were added sequentially 1.37 mL (8.1 mmol) of triethylamine and 0.931 mL (7.5 mmol) of isobutyl chloroformate and the reaction was stirred at this temperature for 15 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 4:1 hexane:ethyl acetate) afforded the title diazoketone.
$^1$H NMR (500 MHz, CDCl$_3$) δ 7.03-6.95 (m, 1H), 6.95-6.88 (m, 2H), 5.43 (bs, 1H), 5.18 (bs, 1H), 4.45 (bs, 1H), 3.19-3.12 (m, 1H), 2.97-2.80 (m, 1H), 1.38 (s, 9H).

Step C: (3R)-3-[(tert-Butoxycarbonyl)amino]-4-(2,5-difluorophenyl)butanoic acid

To a solution of 2.14 g (6.58 mmol) of (R,S)-3-[(tert-butoxycarbonyl)-amino]-1-diazo4-(2,5-difluorophenyl)butan-2-one dissolved in 100 mL of methanol at −30° C. were added sequentially 3.3 mL (19 mmol) of N,N-diisopropylethylamine and 302 mg (1.32 mmol) of silver benzoate. The reaction was stirred for 90 min before diluting with ethyl acetate and washing sequentially with 2N hydrochloric acid, saturated aqueous sodium bicarbonate solution, and brine. The organic phase was dried over magnesium sulfate, concentrated in vacuo and the enantiomers were separated by preparative chiral HPLC (Chiralpak AD column, 5% ethanol in hexanes) to give 550 mg of the desired (R)-enantiomer, which eluted first. This material was dissolved in 50 mL of a mixture of tetrahydrofuran:methanol:1N aqueous lithium hydroxide (3:1:1) and stirred at 50° C. for 4 h. The reaction was cooled, acidified with 5% dilute hydrochloric acid and extracted with ethyl acetate. The combined organic phases were washed with aqueous brine solution, dried over magnesium sulfate and concentrated in vacuo to give the title compound as a white foamy solid.

$^1$H NMR (500 MHz, CDCl$_3$) δ 7.21 (m, 1H), 6.98 (m, 2H), 6.10 (bs, 1H), 5.05 (m, 1H), 4.21 (m, 1H), 2.98 (m, 2H), 2.60 (m, 2H), 1.38 (s, 9H).

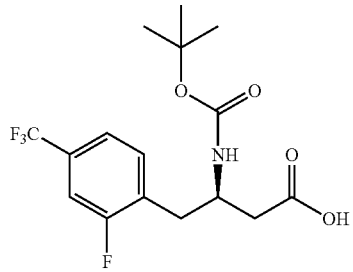

INTERMEDIATE 2

(3R)-3-[(tert-Butoxycarbonyl)amino]-4-[2-fluoro-4-(trifluoromethyl)phenyl]-butanoic acid Step A: (2R,5S)-2,5-Dihydro-3,6-dimethoxy-2-(2'-fluoro-4'-(trifluoromethyl)benzyl)-5-isopropylpyrazine To a solution of 3.32 g (18 mmol) of commercially available (2S)-2,5-dihydro-3,6-dimethoxy-2-isopropylpyrazine in 100 mL of tetrahydrofuran at −70° C. was added 12 mL (19 mmol) of a 1.6M solution of butyllithium in hexanes. After stirring at this temperature for 20 min, 5 g (19.5 mmol) of 2-fluoro-4-trifluoromethylbenzyl bromide in 20 mL of tetrahydrofuran was added and stirring was continued for 3 h before warming the reaction to ambient temperature. The reaction was quenched with water, concentrated in vacuo, and extracted with ethyl acetate. The combined organic phase was washed with brine, dried, and concentrated in vacuo. Purification by flash chromatography (silica gel, 0-5% ethyl acetate in hexanes) afforded the title compound.

$^1$H NMR (500 MHz, CDCl$_3$) δ 7.33-7.25 (m, 3H), 4.35-4.31 (m, 1H), 3.75 (s, 3H), 3.65 (s, 3H), 3.60 (t, 1H, J=3.4 Hz), 3.33 (dd, 1H, J=4.6, 13.5 Hz), 3.03 (dd, 1H, J=7, 13.5 Hz), 2.25-2.15 (m, 1H), 1.0 (d, 3H, J=7 Hz), 0.66 (d, 3H, J=7 Hz).

Step B: (R)-N-tert-Butoxycarbonyl)-2-fluoro-4-trifluoromethyl-phenylalanine methyl ester To a solution of 5.5 g (15 mmol) of (2R,5S)-2,5-dihydro-3,6-dimethoxy-2-(2'-fluoro-4'-(trifluoromethyl)benzyl)-5-isopropylpyrazine in 50 mL of a mixture of acetonitrile:dichloromethane (10:1) was added 80 mL of 1N aqueous trifluoroacetic acid. The reaction was stirred for 6 h and the organic solvents were removed in vacuo. Sodium carbonate was added until the solution was basic (pH greater than 8), and then the reaction was diluted with 100 mL of tetrahydrofuran and 10 g (46 mmol) of di-tert-butyl dicarbonate was added. The resultant slurry was stirred for 16 h, concentrated in vacuo, and extracted with ethyl acetate. The combined organic phase was washed with brine, dried, and concentrated in vacuo. Purification by flash chromatography (silica gel, 20% ethyl acetate in hexanes) afforded the title compound.

$^1$H NMR (500 MHz, CDCl$_3$) δ 7.38-7.28 (m, 3H), 5.10 (bd, 1H), 4.65-3.98 (m, 1H), 3.76 (s, 3H), 3.32-3.25 (m, 1H), 3.13-3.05 (m, 1H), 1.40 (s, 9H).

Step C: (R)-N-(tert-Butoxycarbonyl)-2-fluoro-4-trifluoromethyl)phenyl-alanine

A solution of 5.1 g (14 mmol) of (R,S)-N-(tert-butoxycarbonyl)-2-fluoro-4-trifluoromethyl)phenylalanine methyl ester in 350 mL of a mixture of tetrahydrofuran: methanol: 1N lithium hydroxide (3:1:1) was stirred at 50° C. for 4 h. The reaction was cooled, acidified with 5% hydrochloric acid and extracted with ethyl acetate. The combined organic phases were washed with brine, dried over magnesium sulfate and concentrated in vacuo to give the title compound.

$^1$H NMR (500 MHz, CD$_3$OD) δ 7.45-7.38 (m, 3H), 4.44-4.40 (m, 1H), 3.38-3.33 (m, 1H), 2.98 (dd, 1H, J=9.6, 13.5 Hz), 1.44 (s, 9H).

Step D: (3R)-3-[(tert-Butoxycarbonyl)amino]-4-[2-fluoro-4-trifluoromethyl)-phenyl]butanoic acid To a solution of 3.4 g (9.7 mmol) of the product from Step C in 60 mL of tetrahydrofuran at 0° C. were added sequentially 2.3 mL (13 mmol) of diisopropylethylamine and 1.7 mL (13 mmol) of isobutyl chloroformate and the reaction was stirred at this temperature for 30 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 9:1 hexane: ethyl acetate) afforded 0.5 g of diazoketone. To a solution of 0.5 g (1.33 mmol) of the diazoketone dissolved in 100 mL of methanol at 0° C. were added sequentially 0.7 mL (4 mmol) of diisopropylethylamine and 32 mg (0.13 mmol) of silver benzoate. The reaction was stirred for 2 h before diluting with ethyl acetate and washing sequentially with 2N hydrochloric acid, saturated aqueous sodium bicarbonate solution, and brine. The organic phase was dried over magnesium sulfate, concentrated in vacuo and dissolved in 50 mL of a mixture of tetrahydrofuran:methanol:1N aqueous lithium hydroxide (3:1:1) and stirred at 50° C. for 3 h. The reaction was cooled, acidified with 5% hydrochloric acid and extracted with ethyl acetate. The combined organic phases were washed with brine, dried over magnesium sulfate and concentrated in vacuo to give the title compound as a white foamy solid.

$^1$H NMR (500 MHz, CD$_3$OD): δ 7.47-7.33 (m, 3H), 4.88 (bs, 1H), 4.26-3.98 (m, 1H), 3.06-3.01 (m, 1H), 2.83-2.77 (m, 1H), 2.58-2.50 (m, 2H), 1.29 (s, 9H).

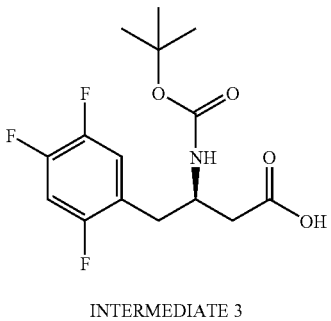

INTERMEDIATE 3

(3R)-3-[(tert-Butoxycarbonyl)amino]-4-(2,4,5-trifluorophenyl)butanoic acid

Step A: (2S, 5R)-2,5-Dihydro-3,6-dimethoxy-2-isopropyl-5-(2',4',5'trifluorobenzyl)-pyrazin The title compound (3.81 g) was prepared from 3.42 g (18.5 mmol) of (2S)-2,5-dihydro-3,6-methoxy-2-isopropylpyrazine and 5 g (22.3 mmol) of 2,4,5-trifluorobenzyl bromide using the procedure described for Intermediate 2, Step A.

$^1$H NMR (500 MHz, CDCl$_3$): δ 7.01 (m, 1H), 6.85 (m, 1H), 4.22 (m, 1H), 3.78 (m, 3H), 3.64 (m, 3H), 3.61 (m, 1H), 3.20 (m, 1H), 2.98 (m, 1H), 2.20 (m, 1H), 0.99 (d, 3H, J=8 Hz), 0.62 (d, 3H, J=8 Hz).

Step B: (R)-N-(tert-Butoxycarbonyl)-2,4,5-trifluorophenylalanine methyl ester

To a solution of 3.81 g (11.6 mmol) of (2S, 5R)-2,5-dihydro-3,6-dimethoxy-2-isopropyl-5-(2',4',5'trifluorobenzyl)pyrazine in 20 mL of acetonitrile was added 20 mL of 2N hydrochloric acid. The reaction was stirred for 72 h and concentrated in vacuo. The residue was dissolved in 30 mL of dichloromethane and 10 mL (72 mmol) of triethylamine and 9.68 g (44.8 mmol) of di-tert-butyl dicarbonate were added. The reaction was stirred for 16 h, diluted with ethyl acetate and washed sequentially with 1N hydrochloric acid and brine. The organic phase was dried over sodium sulfate, concentrated in vacuo and purified by flash chromatography (silica gel, 9:1 hexanes:ethyl acetate) to afford the title compound.

$^1$H NMR (500 MHz, CDCl$_3$): δ 6.99 (m, 1H), 6.94 (m, 1H), 5.08 (m, 1H), 4.58 (m, 1H), 3.78 (m, 3H), 3.19 (m, 1H), 3.01 (m, 1H), 1.41 (s, 9H).

Step C: (R)-N-(tert-Butoxycarbonyl)-2,4,5-trifluorophenylalanine

The title compound (2.01 g) was prepared from 2.41 g (7.5 mmol) of (R)-N-(tert-butoxycarbonyl)-2,4,5-trifluorophenylalanine methyl ester using the procedure described for Intermediate 2, Step C.

LC/MS 220.9 (M+1-BOC).

Step D: (3R)-3-[(tert-Butoxycarbonyl)amino]-4-(2,4,5-trifluorophenyl)-butanoic acid To a solution of 0.37 g (1.16 mmol) of (R)-N-(1,1-diethylethoxy-carbonyl)-2,4,5-trifluorophenylalanine in 10 mL of diethyl ether at −20° C. were added sequentially 0.193 mL (1.3 mmol) of triethylamine and 0.18 mL (1.3 mmol) of isobutyl chloroformate, and the reaction was stirred at this temperature for 15 min. A cooled ethereal solution of diazomethane was then added until the yellow color persisted and stirring was continued for a further 1 h. The excess diazomethane was quenched by dropwise addition of acetic acid, and the reaction was diluted with ethyl acetate and washed sequentially with saturated aqueous sodium bicarbonate solution and brine, dried over magnesium sulfate and concentrated in vacuo. Purification by flash chromatography (silica gel, 3:1 hexane:ethyl acetate) afforded 0.36 g of diazoketone. To a solution of 0.35 g (1.15 mmol) of the diazoketone dissolved in 12 mL of 1,4-dioxane:water (5:1) was added 26 mg (0.113 mmol) of silver benzoate. The resultant solution was sonicated for 2 h before diluting with ethyl acetate and washing sequentially with 1N hydrochloric acid and brine, drying over magnesium sulfate and concentrating in vacuo. Purification by flash chromatography (silica gel, 97:2:1 dichloromethane:methanol:acetic acid) afforded the title compound.

$^1$H NMR (500 MHz, CDCl$_3$): δ 7.06 (m, 1H), 6.95 (m, 1H), 5.06 (bs, 1H), 4.18 (m, 1H), 2.98 (m, 2H), 2.61 (m, 2H), 1.39 (s, 9H).

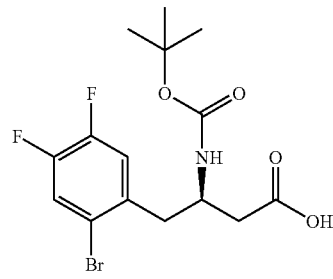

INTERMEDIATE 4

(3R)-4-(2-Bromo-4,5-difluorophenyl)-3-[(tert-butoxycarbonyl)amino]-butanoic acid To a solution of 2.4 g (10 mmol) of 2-bromo-4,5-difluorobenzoic acid [prepared according to the procedure of Braish et al., *Syn. Comm.*, 3067-3074 (1992)] in 75 mL of tetrahydrofuran was added 2.43 g (15 mmol) of carbonyldiimidazole. The solution was heated under reflux for 3.5 h, cooled to ambient temperature and 0.38 g (10 mmol) of sodium borohydride in 15 mL of water was added. The reaction was stirred for 10 min and partitioned between ethyl acetate and 10% aqueous sodium bicarbonate solution. The organic layer was washed twice with warm water, brine, dried over magnesium sulfate, and concentrated in vacuo. Purification by flash chromatography (silica gel, 4:1 hexane:ethyl acetate) afforded 1.9 g of 2-bromo-4,5-difluorobenzyl alcohol. To a solution of 1.9 g (8.4 mmol) of 2-bromo-4,5-difluorobenzyl alcohol in 30 mL of dichloromethane at 0° C. was added 3.4 g (10 mmol) of carbon tetrabromide and 2.7 g (10 mmol) of triphenylphosphine. The reaction was stirred for 2 h at this temperature, the solvent was removed in vacuo and the residue stirred with 100 mL of diethyl ether. The solution was filtered, concentrated in vacuo, and purified by flash chromatography (silica gel, 20:1 hexane:ethyl acetate) to afford 2-bromo-4,5-difluorobenzyl bromide contaminated with carbon tetrabromide which was used without further purification. Using the procedures outlined for the preparation of Intermediates 2-4, the benzyl bromide derivative was converted to the title compound. LC/MS 394 and 396 (M+1).

Essentially following the procedures outlined for the preparation of Intermediates 1-4, the Intermediates in Table 1 were prepared.

TABLE 1

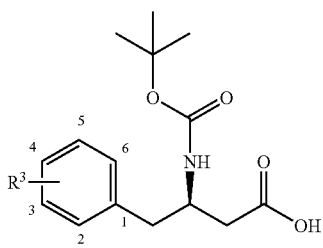

| Intermediate | R³ | Selected ¹H NMR data (CD₃OD) |
|---|---|---|
| 5 | 2-F, 4-Cl, 5-F | 7.11 (dd, 1H, J=8.9, 6.4 Hz), 7.03 (dd, 1H, J=9.0, 6.6) |
| 6 | 2-F, 5-Cl | 7.27 (dd, 1H, J=6.4, 2.5 Hz), 7.21 (m, 1H), 7.03 (t, 1H, J=9.2 Hz) |
| 7 | 2-Me, 5-Cl | 7.16 (d, 1H, J=1.8 Hz), 7.11-7.07 (m, 2H), 2.34 (s, 3H) |
| 8 | 2-Cl, 5-Cl | 7.34 (d, 1H, J=9.0), 7.33 (d, 1H, J=2.1 Hz), 7.21(dd, 1H, J=8.5, 2.5 Hz) |
| 9 | 2-F, 3-Cl, 6-F | 7.35 (td, 1H, J=8.5, 5.8 Hz), 6.95 (t, 1H, J=8.5 Hz) |
| 10 | 3-Cl, 4-F | 7.33 (d, 1H, J=6.9 Hz), 7.19-7.11 (m, 2H) |
| 11 | 2-F, 3-F, 6-F | 7.18-7.12 (m, 1H), 6.91 (m, 1H) |
| 12 | 2-F, 4-F, 6-F | 6.81 (t, 2H, J=8.4 Hz) |
| 13 | 2-OCH₂Ph, 5-F | 7.49 (d, 2H, J=7.6 Hz), 7.38 (t, 2H, J=7.3 Hz), 7.30 (t, 1H, J=7.3Hz), 6.96-6.89 (m, 3H), 5.11(d, 1H, J=11.7 Hz), 5.08 (d, 1H, J=11.9 Hz) |

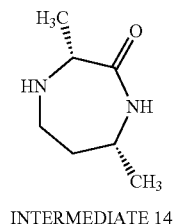

INTERMEDIATE 14

(3R,7R)-3,7-Dimethyl-1,4-diazepan-2-one

Step A: tert-Butyl[(1R)-3-[methoxy(methyl)amino]-1-methyl-3-oxopropyl]carbamate

A solution of (3R)-3-[(tert-butoxycarbonyl)amino]butanoic acid (1 g, 5 mmol) in acetonitrile (40 mL) was treated with 1-[3-(dimethylamino)propyl]-3-ethylcarbodiimide hydrochloride (EDC; 1.05 g, 5.5 mmol), 1-hydroxybenzotriazole (HOBt; 810 mg, 6 mmol), N,O-dimethylhydroxylamine hydrochloride (1.0 g, 10 mmol) and triethylamine (1.4 mL) and stirred at room temperature for 2 d. The solution was evaporated and the residue purified by flash chromatography on a Biotage® system (silica gel, 40-90% ethyl acetate/hexane gradient) to yield the desired product as a colorless viscous oil. MS 269.1 (M+Na).

Step B: tert-Butyl[(1R)-1-methyl-3-oxopropyl]carbamate

Lithium aluminum hydride (5 mL, 1.0M in THF) was added slowly to a stirred solution of tert-butyl[(1R)-3-[methoxy(methyl)amino]-1-methyl-3-oxopropyl]carbamate in tetrahydrofuran (25 mL) at −40° C. under a nitrogen atmosphere. After 30 min, the reaction mixture was quenched with saturated aqueous ammonium chloride solution. The cooling bath was removed and stirring was continued for one hour. The mixture was filtered through a pad of Celite and washed with ether. The filtrate was washed sequentially with ice cold 1N hydrochloric acid, saturated aqueous sodium bicarbonate solution, and brine, dried over magnesium sulfate, filtered and evaporated to yield the title compound as a colorless oil. MS 87.9 (M-Boc+1).

Step C: Methyl N-[(3R)-3-[tert-butoxycarbonyl)amino]butyl]-D-alaninate

A solution of tert-butyl[(1R)-1-methyl-3-oxopropyl]carbamate (0.75 g, 3.65 mmol) in ethanol (25 mL) was treated with D-alanine methyl ester hydrochloride (0.5 g, 3.57 mmol), borane-pyridine (0.5 mL, 8M) and potassium carbonate (0.5 g, 3.62 mmol), and the reaction mixture was stirred overnight. The resultant white precipitate was filtered and washed with chloroform. The filtrate was evaporated and used in the next step without further purification. MS 175.1 (M−Boc+1).

Step D: Methyl N-[(benzyloxy)carbonyl]-N-[(3R)-3-[tert-butoxycarbonyl)amino]butyl]-D-alaninate A solution of methyl N-[(3R)-3-[tert-butoxycarbonyl)amino]butyl]-D-alaninate obtained from the previous step in THF (30 mL) was treated with N-benzyloxycarbonyloxysuccinimide (0.99 g, 3.6 mmol) and stirred overnight at room temperature. Solvent was removed and the residue purified by flash chromatography on a Biotage® system (silica gel, 10-75% ethyl acetate/hexane gradient) to yield the title compound as a colorless oil. MS 431.1 (M+Na).

Step E: Methyl N-[(3R)-3-aminobutyl]-N-[(benzyloxy)carbonyl]-D-alaninate

Methyl N-[(benzyloxy)carbonyl]-N-[(3R)-3-[tert-butoxycarbonyl)amino]butyl]-D-alaninate (0.75 g, 1.8 mmol) was stirred at room temperature with 4N hydrogen chloride in dioxane (10 mL) for two h and evaporated. The residue was purified by flash chromatography on a Biotage® system (silica gel, 8% methanol/2N ammonia in dichloromethane) to yield the desired product as a colorless oil. MS 309.1 (M+1).

Step F: Benzyl (2R,5R)-2,5-dimethyl-3-oxo-1,4-diazepane-1-carboxylate

To a solution of methyl N-[(3R)-3-aminobutyl]-N-[(benzyloxy)carbonyl]-D-alaninate (0.5 g, 1.6 mmol) in dichloromethane (65 mL) was added trimethylaluminum (0.8 mL, 2M in toluene) and triethylamine (0.025 mL, 0.16 mmol), and the reaction mixture was stirred overnight at room temperature. Celite was added and the reaction was quenched by the dropwise addition of saturated aqueous ammonium chloride solution. The white granular solid formed was filtered and washed with dichloromethane. The filtrate was evaporated and purified by flash chromatography on a Biotage® system (silica gel, 5% methanol/dichloromethane) to yield the title compound. MS 277.2 (M+1).

Step G: (3R,7R)-3,7-Dimethyl-1,4-diazepan-2-one

A mixture of benzyl (2R,5R)-2,5-dimethyl-3-oxo-1,4-diazepane-1-carboxylate (160 mg) and 10% palladium on carbon (32 mg) in methanol (15 mL) was stirred at room temperature overnight, filtered over Celite, and washed with 10% methanol in dichloromethane. The filtrate was concentrated under reduced pressure to yield the title compound. MS 143.1 (M+1).

Essentially following the methods described for the preparation of Intermediate 14 above, the intermediates listed in Table 2 were prepared.

TABLE 2

| Intermediate | R⁴ | R⁶ | MS (M + 1) |
|---|---|---|---|
| 15 | 2-pyridyl-CH$_2$ | CH$_3$ | 220.2 |
| 16 | H | 2-F-phenyl-CH$_2$ | 223.2 |
| 17 | CH$_3$ | 2-F-phenyl-CH$_2$ | 237.7 |
| 18 | CH$_3$ | CF$_3$ | 197.2 |
| 19 | 2-F-phenyl-CH$_2$ | CH$_3$ | 237.2 |
| 20 | CF$_3$CH$_2$ | CH$_3$ | 211.2 |
| 21 | 2-Me-phenyl-CH$_2$ | CH$_3$ | 233.2 |
| 22 | 2-CF$_3$-phenyl-CH$_2$ | CH$_3$ | 287.3 |

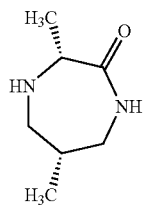

INTERMEDIATE 23

(3R,6R)-Hexahydro-3,6-dimethyl-2H-1,4-diazepin-2-one

Step A:
3-[(tert-Butoxycarbonyl)amino]-2-methylpropanoic acid

A solution of di-tert-butyl dicarbonate (22 mL, 22 mmol, 1M in THF) was added to a stirred solution of DL-3-aminoisobutyric acid (2.06 g, 20 mmol) and potassium carbonate (3.0 g, 22 mmol) in water (30 mL) and stirred at room temperature overnight. The aqueous mixture was washed with ether and then carefully acidified (pH~2) with 3N hydrochloric acid at 0° C., and the resulting cloudy mixture was extracted with ethyl acetate (3x). The combined organic layer was washed with brine, dried over sodium sulfate, filtered, and evaporated to yield 3-[(tert-butoxycarbonyl)amino]-2-methylpropanoic acid as white solid.

Step B: tert-Butyl {3-[methoxy(methyl)amino]-2-methyl-3-oxopropyl}carbamate

3-[(tert-Butoxycarbonyl)amino]-2-methylpropanoic acid (2.0 g, 9.9 mmol) was dissolved in acetonitrile (50 mL). To this solution was added HOBT (1.6 g, 11.85 mmol) and EDC (2.0 g, 10.4 mmol). The reaction was stirred at room temperature for 2 hr, and then treated with triethylamine (2.8 mL, 20 mmol) and N,O-dimethylhydroxyamine hydrochloride (2.0 g, 20 mmol). The reaction mixture was stirred at room temperature overnight. The reaction was quenched with water and extracted with ethyl acetate (3x). The combined organic extract was washed sequentially with 0.5N hydrochloric acid, 1N aqueous sodium bicarbonate solution and brine, dried over sodium sulfate, filtered and evaporated. The crude product was purified by flash chromatography on a Biotage® system (silica, 40-100% ethyl acetate in hexanes) to yield tert-butyl {3-[methoxy(methyl)amino]-2-methyl-3-oxopropyl}carbamate as white solid. MS (M+1−Boc): 147.

Step C: tert-Butyl (2-methyl-3-oxopropyl)carbamate

A solution of LAH (10 mL, 10 mmol, 1M in THF) was slowly added over ~15 min to a stirred solution of tert-butyl {3-[methoxy(methyl)amino]-2-methyl-3-oxopropyl}carbamate (2.2 g, 8.9 mmol) in THF (40 mL) at −40° C. under nitrogen. After stirring at −40° for 30 min, the reaction mixture was quenched carefully by dropwise addition of saturated aqueous sodium bisulfate solution and stirred at room temperature for 1 hr. The mixture was filtered through Celite, and the filtrate was washed sequentially with ice-cold 1N hydrochloric acid (2x), saturated aqueous sodium bicarbonate and brine, dried over magnesium sulfate, filtered and concentrated to yield tert-butyl (2-methyl-3-oxopropyl)carbamate as colorless viscous oil. MS (M+1−Boc): 88.0

Step D: Methyl N-{3-[(tert-butoxycarbonyl)amino]-2-methylpropyl}-D-alaninate

To a stirred solution of tert-butyl (2-methyl-3-oxopropyl) carbamate (2.0 g, 8.9 mmol) in ethanol was added D-Alanine methyl ester hydrochloride (1.25 g, 8.9 mmol), followed by potassium carbonate (0.62 g, 4.5 mmol). The resulting mixture was stirred at room temperature for 3 hr. Sodium cyanoborohydride (0.63 g, 10 mmol) was added in one portion. The reaction mixture was stirred at room temperature overnight. The solvent was removed on a rotavap, and the residue was taken up into water and extracted with ethyl acetate (3x). The combined organic extract was washed with brine, dried over sodium sulfate and evaporated to yield methyl N-{3-[(tert-butoxycarbonyl)amino]-2-methylpropyl}-D-alaninate as colorless viscous oil, which was used without further purification. MS (M+1−Boc): 175.3

Step E: Methyl N-[(benzyloxy)carbonyl]-N-{3-[(tert-butoxycarbonyl)amino]-2-methylpropyl}-D-alaninate To a stirred solution of methyl N-{3-[(tert-butoxycarbonyl)amino]-2-methylpropyl}-D-alaninate (2.5 g, ~8.9 mmol) in dichloromethane (50 mL) was added Cbz-OSu (2.25 g, 9.0 mmol). The resulting mixture was stirred at room temperature for 3 days. The solvent was removed on a rotavap, and the crude product was purified by flash chromatography on a Biotage® system (silica, 25-80% ethyl acetate in hexanes) to yield methyl N-[(benzyloxy)carbonyl]-N-{3-[(tert-butoxycarbonyl)amino]-2-methylpropyl}-D-alaninate as colorless viscous oil. MS (M+1−Boc): 309.4

Step F: Methyl N-(3-amino-2-methylpropyl)-N-[(benzyloxy)carbonyl]-D-alaninate

Methyl N-[(benzyloxy)carbonyl]-N-{3-[(tert-butoxycarbonyl)amino]-2-methylpropyl}-D-alaninate (1.6 g, 3.9 mmol) was treated with 4N hydrogen chloride in dioxane (10 mL) at room temperature for 2 hr. The solvent was removed under a stream of nitrogen, and the crude product was purified by flash chromatography on a Biotage® system (silica, 7% pre-mixed 2N ammonia/methanol in dichloromethane) to yield methyl N-(3-amino-2-methylpropyl)-N-[(benzyloxy)carbonyl]-D-alaninate as colorless viscous oil. MS (M+1): 309.4

Step G: Benzyl (2R,6S)-hexahydro-2,6-dimethyl-3-oxo-1H-1,4-diazepine-1-carboxylate and benzyl (2R,6R)-hexahydro-2,6-dimethyl-3-oxo-1H-1,4-diazepine-1-carboxylate To a stirred solution of methyl N-(3-amino-2-methylpropyl)-N-[(benzyloxy)carbonyl]-D-alaninate (0.6 g, 2.0 mmol) in dichloromethane (60 mL) was added a 2M solution of tert-butylmagnesium chloride in ether (1.0 mL, 2 mmol), and reaction was stirred at room temperature under nitrogen overnight. More magnesium reagent (1 mL, 2 mmol) was added and the reaction was continued for another day, and then quenched by addition of Celite followed by saturated aqueous sodium sulfate. The mixture was stirred for 30 min and filtered. The filtrate was evaporated. The crude product was purified by flash chromatography on a Biotage® system (silica, 60-100% ethyl acetate in hexanes) to yield two diastereomers: the faster eluting benzyl (2R, 6S)-hexahydro-2,6-dimethyl-3-oxo-1H-1,4-diazepine-1-carboxylate and the slower eluting benzyl (2S,6R)-hexahydro-2,6-dimethyl-3-oxo-1H-1,4-diazepine-1-carboxylate, both as yellow viscous oils. MS (M+1): 277.3; 277.3 respectively.

Step H: (3R,6R)-Hexahydro-3,6-dimethyl-2H-1,4-diazepin-2-one

A solution of benzyl (2R,6S)-hexahydro-2,6-dimethyl-3-oxo-1H-1,4-diazepine-1-carboxylate (220 mg, 0.8 mmol) in ethanol (10 mL) was stirred at room temperature overnight under a hydrogen balloon, using Pd/C (30 mg) as catalyst. The catalyst was filtered over Celite and washed with 10% methanol in dichloromethane. The solvent was removed to yield (3R,6R)-hexahydro-3,6-dimethyl-2H-1,4-diazepin-2-one as white crystalline solid. MS (M+1): 143.1

The intermediates in Table 3 were made by essentially similar methods as described for the synthesis of Intermediate 23.

TABLE 3

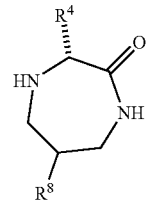

| Intermediate | $R^4$ | $R^8$ | MS (M + 1) |
|---|---|---|---|
| 24 | Me | (S)-Me | 143 |
| 25 | Et | (R)-Me | 157 |
| 26 | Et | (S)-Me | 157 |

TABLE 3-continued

| Intermediate | $R^4$ | $R^8$ | MS (M + 1) |
|---|---|---|---|
| 27 | $CH_2CF_3$ | (R)-Me | 211 |
| 28 | $CH_2CF_3$ | (S)-Me | 211 |

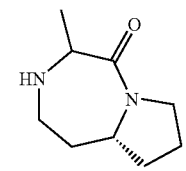

INTERMEDIATE 29

(9aR)-4-Methyloctahydro-5H-pyrrolo[1,2-d][1,4]diazepin-5-one

Step A: [(2R)-1-(carbo-tert-butyloxy)pyrrolidin-2-yl]acetonitrile

To a stirred solution of (R)-N-Boc-Prolinol (4.33 g, 20 mmol) in dichloromethane (100 mL) was added triethylamine (3.4 mL, 24 mmol), 4-dimethylaminopyridine (250 mg, 2 mmol), and p-toluene sulfonylchloride (4.0 g, 20 mmol). The solution was stirred at room temperature for 24 hr and washed sequentially with cold (0° C.) 1N hydrochloric acid, saturated aqueous sodium bicarbonate solution and brine. The organic layer was dried over anhydrous sodium sulfate and concentrated to yield a viscous yellow oil. The product obtained as such was taken up in N,N-dimethyl formamide (40 mL), stirred at room temperature with sodium cyanide for seven days, heated at 80° C. for 24 hr, and then partitioned between ethyl acetate and 1N aqueous sodium bicarbonate solution. After the usual aqueous workup, the crude product was purified by flash chromatography on a Biotage® system (silica, gradient 5-60% ethyl acetate in hexanes) to yield [(2R)-1-(carbo-tert-butyloxy)pyrrolidin-2-yl]acetonitrile as slightly yellowish oil.

Step B: [(2R)-1-pyruvoylpyrrolidin-2-yl]acetonitrile

[(2R)-1-(carbo-tert-butyloxy)pyrrolidin-2-yl]acetonitrile (1.0 g, 4.75 mmol) was stirred in TFA and dichloromethane (1:1 mixture, 12 mL) at room temperature for 3 hr. The solvent was removed under reduced pressure and the residue was taken up in acetonitrile (25 mL). To this solution was added pyruvic acid (450 mg, 5.0 mmol), followed by HOBT (0.8 g, 6 mmol), EDC (1.0 g, 5.5 mmol), and triethylamine (1.0 mL, 7.0 mmol). The reaction was stirred at room temperature overnight. After removal of solvent, the crude product was purified by flash chromatography on a Biotage® system (silica, 30-90% ethyl acetate in hexanes) to yield [(2R)-1-pyruvoylpyrrolidin-2-yl]acetonitrile as yellow oil. MS (M+Na): 203.2

Step C: (9aR)-4-methyloctahydro-5H-pyrrolo[1,2-d][1,4]diazepin-5-one

[(2R)-1-pyruvoylpyrrolidin-2-yl]acetonitrile (250 mg, 1.38 mmol) was dissolved in ethanol (30 mL). The reaction was stirred under a hydrogen balloon at room temperature in presence of platinum oxide (25 mg) and chloroform (0.25 mL) for 3 days. Catalyst was filtered over Celite and washed with 10% methanol in dichloromethane. The combined organic layer was evaporated and crude product was purified by flash chromatography on a Biotage® system (silica, 5-60% ethyl acetate in hexanes) to yield the diastereomeric mixture 4-methyloctahydro-5H-pyrrolo[1,2-d][1,4]diazepin-5-ones as a slightly yellowish oil. MS (M+1-Boc): 169.2.

EXAMPLE 1

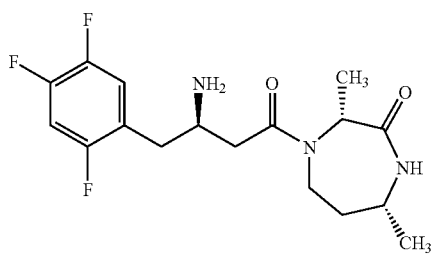

(3R,7R)-4-[(3R)-3-Amino-4-(2,4,5-trifluorophenyl)butanoyl]-3,7dimethyl-1,4-diazepan-2-one Step A: (3R,7R)-4-[(3R)-3-[(tert-Butoxycarbonyl)amino]-4-(2,4,5-trifluorophenyl)butanoyl]-3,7-dimethyl-1,4-diazepan-2-one Isobutyl chloroformate (0.085 mL, 0.63 mmol) was added to a solution of (3R)-3-[(tert-butoxycarbonyl)amino]-4-(2,4,5-trifluorophenyl)butanoic acid (Intermediate 3, 210 mg, 0.63 mmol) and N-methylmorpholine (0.080 mL, 0.7 mmol) in 10 mL of dichloromethane at −20 to −30° C. and the resultant mixture was stirred for 1 h. A solution of (3R,7R)-3,7-dimethyl-1,4-diazepan-2-one in dichloromethane (5 mL) was added to the above solution. The reaction mixture was allowed to warm up to room temperature and stirring was continued overnight. The solution was subjected directly to flash chromatography on a Biotage® system (silica gel, 5% methanol/dichloromethane) to yield the title compound as a white solid. MS 358 (M−Boc+1).

Step B: (3R,7R)-4-[(3R)-3-Amino-4-(2,4,5-trifluorophenyl)butanoyl]-3,7-dimethyl-1,4-diazepan-2-one, hydrochloride A solution of (3R,7R)-4-[(3R)-3-[(tert-butoxycarbonyl)amino]-4-(2,4,5-trifluorophenyl)butanoyl]-3,7-dimethyl-1,4-diazepan-2-one (175 mg, 0.38 mmol) in 4 mL of 4N hydrogen chloride in dioxane (4 mL, 4N) was stirred for 2 h and concentrated. The residue was dried under vacuum overnight to yield the title compound as a white solid. MS 358.2 (M+1).

Essentially following the procedure described for Example 1, the Examples listed in Table 4 were prepared.

TABLE 4

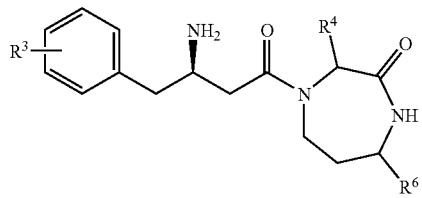

| Ex. | $R^3$ | $R^4$ | $R^6$ | MS (M + 1) |
|---|---|---|---|---|
| 2 | 2-F, 4-F, 5-F | 2-pyridyl-$CH_2$ | $CH_3$ | 435.2 |
| 3 | 2-F, 4-F, 5-F | H | 2-F-phenyl-$CH_2$ | 438.3 |
| 4 | 2-F, 4-F, 5-F | $CH_3$ | 2-F-phenyl-$CH_2$ | 452.3 |
| 5 | 2-F, 4-F, 5-F | $CH_3$ | $CF_3$ | 412.3 |
| 6 | 2-F, 4-F, 5-F | 2-F-phenyl-$CH_2$ | $CH_3$ | 452.3 |
| 7 | 2-F, 4-F, 5-F | $CF_3CH_2$ | $CH_3$ | 426.3 |
| 8 | 2-F, 4-F, 5-F | 2-Me-phenyl-$CH_2$ | $CH_3$ | 448.3 |
| 9 | 2-F, 4-F, 5-F | 2-$CF_3$-phenyl-$CH_2$ | $CH_3$ | 502.4 |

EXAMPLE 10

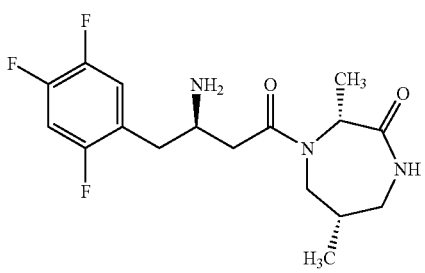

3R,6S)-4-[(3R)-3-Amino-4-(2,4,5-trifluorophenyl)butanoyl]hexahydro-3,6-dimethyl-2H-1,4-diazepin-2-one Step A: (3R,6S)-4-[(3R)-3-[(tert-Butoxycarbonyl)amino]-4-(2,4,5-trifluorophenyl)butanoyl]hexahydro-3,6-dimethyl-2H-1,4-diazepin-2-one To a stirred solution of (3R)-3-[(tert-butoxycarbonyl)amino]-4-(2,4,5-trifluorophenyl)butanoic acid (Intermediate 3, 120 mg, 0.36 mmol) in acetonitrile (10 mL) was added HOBT (60 mg, 0.43 mmol) and EDC (75 mg, 0.4 mmol). The reaction was stirred at room temperature for 1 h and then treated with (3R,6R)-hexahydro-3,6-dimethyl-2H-1,4-diazepin-2-one (Intermediate 23, 50 mg, 0.35 mmol). The reaction was stirred at room temperature overnight. After removal of solvent, the crude product was purified by flash chromatography on a Biotage® system (silica, 6% methanol in dichloromethane) to yield the title compound as white solid. MS (M+1−Boc): 358.0

Step B: (3R,6S)-4-[(3R)-3-Amino-4-(2,4,5-trifluorophenyl)butanoyl]hexahydro-3,6-dimethyl-2H-1,4-diazepin-2-one hydrochloride (3R,6S)-4-[(3R)-3-[(tert-Butoxycarbonyl)amino]-4-(2,4,5-trifluorophenyl)butanoyl]hexahydro-3,6dimethyl-2H-1,4- diazepin-2-one (135 mg, 0.3 mmol) was treated with 4N hydrogen chloride in dioxane (2 mL) at room temperature for 2 hr. The solvent was removed under a stream of nitrogen, and the crude product was purified on preparative TLC plates (silica, 10% 2N ammonia/methanol in dichloromethane) to yield the title compound as white solid. MS (M+1): 358.2.

The following examples were made by essentially following similar methods described for the synthesis of Example 10.

TABLE 5

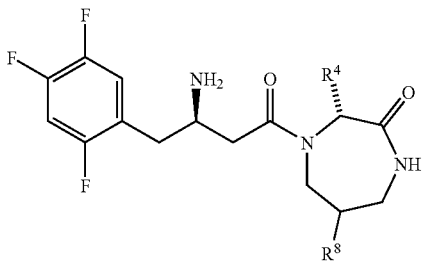

| Example | $R^4$ | $R^8$ | MS (M + 1) |
|---|---|---|---|
| 11 | Me | (R)-Me | 358.1 |
| 12 | Et | (S)-Me | 372.0 |
| 13 | Et | (R)-Me | 372.1 |
| 14 | $CH_2CF_3$ | (S)-Me | 425.9 |
| 15 | $CH_2CF_3$ | (R)-Me | 425.9 |

EXAMPLE 16

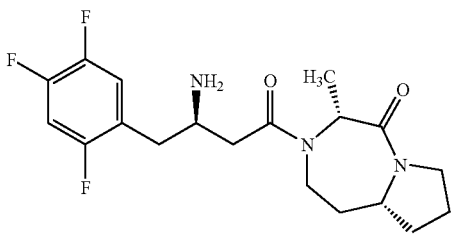

(4R,9aR)-3-[(3R)-3-Amino-4-(2,4,5-trifluorophenyl)butanoyl]-4-methyloctahydro-5H-pyrrolo[1,2-d][1,4]diazepin-5-one Following the procedures outlined for the synthesis of Example 10, the title compound was prepared from Intermediate 29. Prior to deprotection, the two diastereomers were separated on a ChiralCell OD Column eluting with 10% ethanol in hexanes. The slower eluting diastereomer, tert-butyl[(1R)-3-[(4R,9aR)-4methyl-5-oxooctahydro-3H-pyrrolo[1,2-d][1,4]diazepin-3-yl]-3-oxo-1-(2,4,5-trifluorobenzyl)propyl]carbamate was carried on to the final product. MS (M+1): 384.4

Example of a Pharmaceutical Formulation

As a specific embodiment of an oral pharmaceutical composition, a 100 mg potency tablet is composed of 100 mg of any of the compounds of the present invention, 268 mg microcrystalline cellulose, 20 mg of croscarmellose sodium and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the formula I:

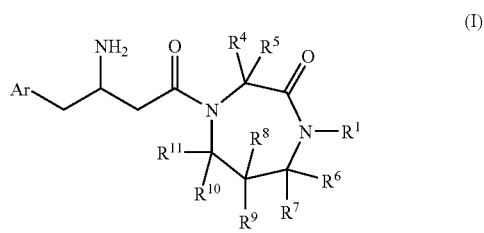

(I)

or a pharmaceutically acceptable salt thereof; wherein each n is independently 0, 1, or 2;
Ar is phenyl substituted with one to five $R^3$ substituents;
$R^1$ is selected from the group consisting of hydrogen,
  $C_{1-10}$ alkyl, wherein alkyl is unsubstituted or substituted with one to five substituents independently selected from halogen, hydroxy, $C_{1-6}$ alkoxyl, carboxy, $C_{1-6}$ alkyloxycarbonyl, and phenyl-$C_{1-3}$ alkoxy, wherein alkoxy is unsubstituted or substituted with one to five halogens,
  $(CH_2)_n$-aryl, wherein aryl is unsubstituted or substituted with one to five substituents independently selected from halogen, CN, hydroxy, $R^2$, $OR^2$, $NHSO_2R^2$, $NR^2SO_2R^2$, $SO_2R^2$, $CO_2H$, and $C_{1-6}$ alkyloxycarbonyl,
  $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens,
  $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
  $(CH_2)_n$-$C_{3-6}$ cycloalkyl, wherein cycloalkyl is unsubstituted or substituted with one to three substituents independently selected from halogen, hydroxy, $C_{1-6}$ alkyl, and C$_{1-6}$ alkoxy, wherein alkyl and alkoxy are unsubstituted or substituted with one to five halogens; and wherein any methylene (CH$_2$) carbon atom in (CH$_2$)$_n$ is unsubstituted or substituted with one to two groups independently selected from halogen, hydroxy, and C$_{1-4}$ alkyl unsubstituted or substituted with one to five halogens;

each R$^3$ is independently selected from the group consisting of
hydrogen,
halogen,
cyano,
hydroxy,
C$_{1-6}$ alkyl, unsubstituted or substituted with one to five halogens,
C$_{1-6}$ alkoxy, unsubstituted or substituted with one to five halogens,
carboxy,
alkoxycarbonyl,
amino,
NHR$^2$,
NR$_2$R$^2$,
NHSO$_2$R$^2$,
NR$^2$SO$_2$R$^2$,
NHCOR$^2$,
NR$^2$COR$^2$,
NHCO$_2$R$^2$,
NR$^2$CO$_2$R$^2$,
SO$_2$R$^2$,
SO$_2$NH$_2$,
SO$_2$NHR$^2$, and
SO$_2$NR$^2$R$^2$;

each R$^2$ is independently C$_{1-6}$ alkyl, unsubstituted or substituted with one to five substituents independently selected from halogen, CO$_2$H, and C$_{1-6}$ alkyloxycarbonyl;

R$^4$, R$^6$, and R$^{10}$ are each independently selected from the group consisting of:
hydrogen,
cyano,
carboxy,
C$_{1-6}$ alkyloxycarbonyl,
C$_{1-10}$ alkyl, unsubstituted or substituted with one to five substituents independently selected from halogen, hydroxy, C$_{1-6}$ alkoxy, carboxy, C$_{1-6}$ alkyloxycarbonyl, and phenyl-C$_{1-3}$ alkoxy, wherein alkoxy is unsubstituted or substituted with one to five halogens,
(CH$_2$)$_n$-aryl, wherein aryl is unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens,
(CH$_2$)$_n$-heteroaryl, wherein heteroaryl is unsubstituted or substituted with one to three substituents independently selected from hydroxy, halogen, C$_{1-6}$ alkyl, and C$_{1-6}$ alkoxy, wherein alkyl and alkoxy are unsubstituted or substituted with one to five halogens,
(CH$_2$)$_n$-heterocyclyl, wherein heterocyclyl is unsubstituted or substituted with one to three substituents independently selected from oxo, hydroxy, halogen, C$_{1-6}$ alkyl, and C$_{1-6}$ alkoxy, wherein alkyl and alkoxy are unsubstituted or substituted with one to five halogens.
(CH$_2$)$_n$-C$_{3-6}$ cycloalkyl, wherein cycloalkyl is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens, (CH$_2$)$_n$CONR$^{12}$R$^{13}$, wherein R$^{12}$ and R$^{13}$ are independently selected from the group consisting of hydrogen, tetrazolyl, thiazolyl, (CH$_2$)$_n$-phenyl, (CH$_2$)$_n$—C$_{3-6}$ cycloalkyl, and C$_{1-6}$ alkyl, wherein alkyl is unsubstituted or substituted with one to five halogens and wherein phenyl and cycloalkyl are unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens; or wherein R$^{12}$ and R$^{13}$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens;

and wherein any methylene (CH$_2$) carbon atom in (CH$_2$)$_n$ is unsubstituted or substituted with one to two groups independently selected from halogen, hydroxy, and C$_{1-4}$ alkyl unsubstituted or substituted with one to five halogens;

R$^8$ is selected from the group consisting of halogen, hydroxy, and R$^4$;

R$^5$, R$^7$ and R$^{11}$ are each independently hydrogen or C$_{1-6}$ alkyl; or wherein R$^7$ and R$^1$ together with the nitrogen atom to which R$^1$ is attached form a heterocyclic ring selected from azetidine, pyrrolidine and piperidine wherein said heterocyclic ring is unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens; and R$^9$ is selected from the group consisting of hydrogen, hydroxy, halogen, or C$_{1-6}$ alkyl; with the proviso that at least one of R$^6$, R$^7$, R$^8$ and R$^9$ is not hydrogen.

2. The compound of claim 1 of the formula Ia:

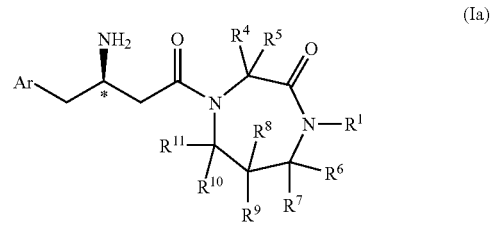

wherein the carbon atom marked with an * has the R configuration.

3. The compound of claim 1 wherein R$^3$ is selected from the group consisting of hydrogen, fluoro, chloro, bromo, trifluoromethyl, and methyl.

4. The compound of claim 3 wherein R$^3$ is hydrogen, chloro, or fluoro.

5. The compound of claim 1 wherein R$^1$ is selected from the group consisting of
hydrogen,
C$_{1-6}$ alkyl, wherein alkyl is unsubstituted or substituted with one to five substituents independently selected from halogen, hydroxy, $C_{1-6}$ alkoxy, carboxy, $C_{1-6}$ alkyloxycarbonyl, and phenyl-$C_{1-3}$ alkoxy, wherein alkoxy is unsubstituted or substituted with one to five halogens, and $(CH2)_n$-$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens; and wherein any methylene ($CH_2$) carbon atom in $CCH_2)_n$ is unsubstituted or substituted with one to two groups independently selected from halogen, hydroxy, and $C_{1-4}$ alkyl unsubstituted or substituted with one to five halogens.

6. The compound of claim 5 wherein $R^1$ is selected from the group consisting of hydrogen, methyl, and cyclopropyl.

7. The compound of claim 6 wherein $R^1$ is hydrogen.

8. The compound of claim 1 wherein $R^4$ is selected from the group consisting of:

hydrogen, $C_{1-6}$ alkyl, unsubstituted or substituted with one to five substituents independently selected from halogen, hydroxy, $C_{1-6}$ alkoxy, carboxy, $C_{1-6}$ alkyloxycarbonyl, and phenyl-$C_{1-3}$ alkoxy, wherein alkoxy is unsubstituted or substituted with one to five halogens, $(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, $(CH_2)_n$-$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens; and wherein any methylene ($CH_2$) carbon atom in $(CH_2)_n$ is unsubstituted or substituted with one to two groups independently selected from halogen, hydroxy, and $C_{1-4}$ alkyl unsubstituted or substituted with one to five halogens.

9. The compound of claim 8 wherein $R^4$ is selected from the group consisting of:

hydrogen, $CH_3$, $CH_2CH_3$, $CH_2CF_3$, $CH_2$(2-pyridyl), $CH_2Ph$, $CH_2$(2-F-Ph), $CH_2$(2-Me-Ph), and $CH_2$(2-$CF_3$-Ph).

10. The compound of claim 1 wherein $R^6$ is selected from the group consisting of:

hydrogen, $C_{1-6}$ alkyl, unsubstituted or substituted with one to five substituents independently selected from halogen, hydroxy, $C_{1-6}$ alkoxy, carboxy, $C_{1-6}$ alkyloxycarbonyl, and phenyl-$C_{1-3}$ alkoxy, wherein alkoxy is unsubstituted or substituted with one to five halogens, $(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, $(CH_2)_n$-$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens; and wherein any methylene ($CH_2$) carbon atom in $(CH_2)_n$ is unsubstituted or substituted with one to two groups independently selected from halogen, hydroxy, and $C_{1-6}$ alkyl unsubstituted or substituted with one to five halogens.

11. The compound of claim 10 wherein $R^6$ is selected from the group consisting of:

hydrogen, $C_{1-6}$ alkyl, unsubstituted or substituted with one to five substituents independently selected from halogen, hydroxy, $C_{1-6}$ alkoxy, carboxy, $C_{1-6}$ alkyloxycarbonyl, and phenyl-$C_{1-3}$ alkoxy, wherein alkoxy is unsubstituted or substituted with one to five halogens, and $(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; and wherein methylene ($CH_2$) carbon atom in $(CH_2)_n$ is unsubstituted or substituted with one to two groups independently selected from halogen, hydroxy, and $C_{1-4}$ alkyl unsubstituted or substituted with one to five halogens.

12. The compound of claim 11 wherein $R^6$ is selected from the group consisting of:

hydrogen, $CH_3$, $CH_2CH_3$, $CF_3$, $CH_2Ph$, and $CH_2$(2-F-Ph).

13. The compound of claim 1 wherein $R^8$ is selected from the group consisting of hydrogen, hydroxy, halogen, and $C_{1-6}$ alkyl, unsubstituted or substituted with one to five substituents independently selected from halogen, hydroxy, $C_{1-6}$ alkoxy, carboxy, $C_{1-6}$ alkyloxycarbonyl, and phenyl-$C_{1-3}$ alkoxy, wherein alkoxy is unsubstituted or substituted with one to five halogens.

14. The compound of claim 13 wherein $R^8$ is hydrogen.

15. The compound of claim 1 wherein $R^{10}$ is selected from the group consisting of:

hydrogen, and $C_{1-6}$ alkyl, unsubstituted or substituted with one to five substituents independently selected from halogen, hydroxy, $C_{1-6}$ alkoxy, carboxy, $C_{1-6}$ alkyloxycarbonyl, and phenyl-$C_{1-3}$ alkoxy, wherein alkoxy is unsubstituted or substituted with one to five halogens.

16. The compound of claim 15 wherein $R^{10}$ is hydrogen.

17. The compound of claim 1 wherein $R^5$, $R^7$ and $R^{11}$ are each independently selected from hydrogen and methyl.

18. The compound of claim 17 wherein $R^5$, $R^7$ and $R^{11}$ are hydrogen.

19. The compound of claim 1 wherein $R^9$ is selected from hydrogen, halogen and methyl.

20. The compound of claim 19 wherein $R^9$ is hydrogen.

21. The compound of claim 19 wherein $R^9$ is methyl and $R^5$, $R^7$, $R^8$, $R^{10}$, and $R^{11}$ are hydrogen.

22. The compound of claim 21 wherein $R^4$ is selected from the group consisting of:
hydrogen,
$CH_3$,
$CH_2CH_3$,
$CH_2CH_3$,
$CH_2$(2-pyridyl),
$CH_2Ph$,
$CH_2$(2-F-Ph),
$CH_2$(2-Me-Ph), and
$CH_2$(2-$CF_3$-Ph).

23. The compound of claim 1 wherein $R^5$, $R^7$, $R^8$, $R^9$, $R^{10}$, and $R^{11}$ are hydrogen, with the proviso that $R^6$ is not hydrogen.

24. The compound of claim 23 wherein $R^4$ is selected from the group consisting of:
hydrogen,
$CH_3$,
$CH_2CH_3$,
$CH_2CF_3$,
$CH_2$(2-pyridyl),
$CH_2Ph$,
$CH_2$(2-F-Ph),
$CH_2$(2-Me-Ph), and
$CH_2$(2-$CF_3$-Ph); and
$R^6$ is selected from the group consisting of:
$CH_3$,
$CH_2CH_3$,
$CF3$,
$CH_2Ph$, and
$CH_2$(2-F-Ph).

25. The compound of claim 24 wherein $R^1$ is hydrogen.

26. The compound of claim 25 wherein the stereogenic carbon atoms marked with an  and * have the stereochemistry as depicted in formula Ib:

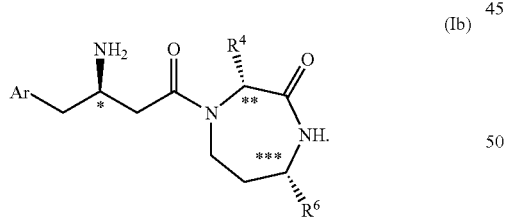

(Ib)

27. The compound of claim 1 wherein $R^7$ and $R^1$ together with the nitrogen atom to which $R^1$ is attached form a heterocyclic ring selected from azetidine, pyrrolidine and piperidine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens.

28. The compound of claim 27 wherein $R^7$ and $R^8$ together with the nitrogen atom to which $R^1$ is attached form a pyrrolidine ring.

29. The compound of claim 28 wherein $R^4$ is selected from the group consisting of:
hydrogen,
$CH_3$,
$CH_2CH_3$,
$CH_2CF_3$,
$CH_2$(2-pyridyl),
$CH_2Ph$,
$CH_2$(2-F-Ph),
$CH_2$(2-Me-Ph), and
$CH_2$(2-$CF_3$-Ph).

30. A compound selected from the group consisting of:

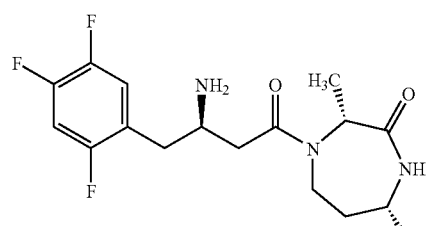

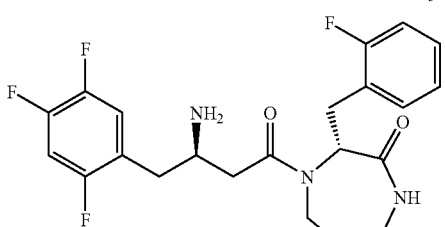

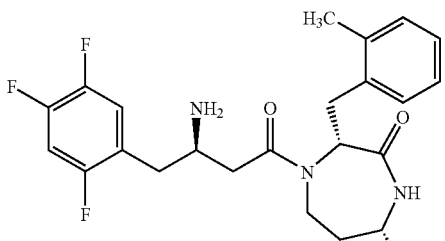

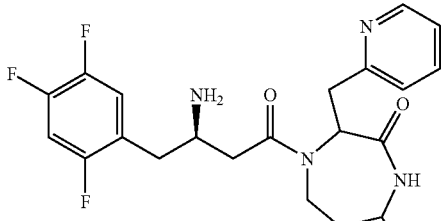

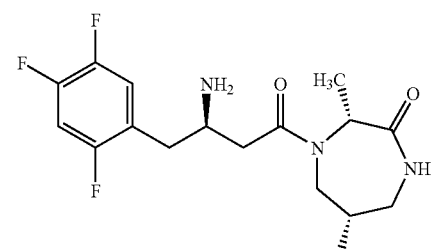

-continued
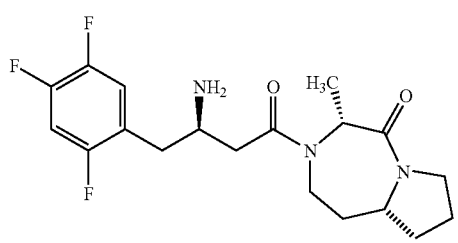
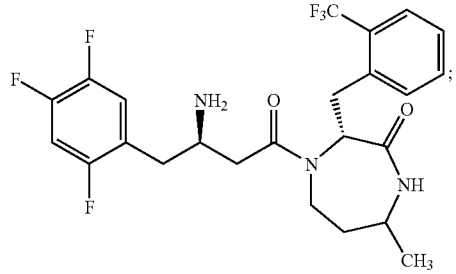
or a pharmaceutically acceptable salt thereof.
31. A pharmaceutical composition which comprises a compound of claim 1 and a pharmaceutically acceptable carrier.
32. A method of treating Type 2 diabetes in a mammal in need thereof which comprises the administration to the mammal of a therapeutically effective amount of a compound of claim 1.
* * * * *